US007892752B2

(12) United States Patent
Dwek et al.

(10) Patent No.: US 7,892,752 B2
(45) Date of Patent: *Feb. 22, 2011

(54) GLYCOSYLATION MARKERS FOR CANCER DIAGNOSING AND MONITORING

(76) Inventors: Raymond A. Dwek, Ambleside, Vernon Avenue, Oxford (GB) OX2 9AU; Umi Marshida Abd Hamid, 49 Summertown House, 369 Banbury Road, Oxford (GB) OX2 7RA; Rafael de Llorens, Francesc Macià 2, 1-3, 17820 Banyoles (ES); Rosa Peracaula, Castell de Perelada 18, 3-3, 17003 Girona (ES); Catherine M. Radcliffe, 175 Kidmore Road, Caversham, Reading (GB) RG4 7NN; John Robertson, 16 Barratt Lane, Attenborough, Beeston (GB) NG9 6AF; Louise Royle, The Jordans, 5 Drayton Road, Sutton Courtenay, Abingdon, Oxon (GB) OX 14 4AJ; Pauline M. Rudd, 29 Sadlers Court, Abingdon (GB) OX 14 2PA; Nicole Zitzmann, 12 Oswestry Road, Oxford (GB) OX1 4TL ( * ) Notice: Subject to any disclaimer, the term of this patent is extended or adjusted under 35 U.S.C. 154(b) by 0 days.

This patent is subject to a terminal disclaimer.

(21) Appl. No.: 11/411,246

(22) Filed: Apr. 26, 2006

(65) Prior Publication Data
US 2006/0269974 A1   Nov. 30, 2006

Related U.S. Application Data

(60) Provisional application No. 60/674,723, filed on Apr. 26, 2005, provisional application No. 60/674,724, filed on Apr. 26, 2005.

(30) Foreign Application Priority Data

Jun. 24, 2005   (WO) ................. PCT/IB2005/002531
Jun. 24, 2005   (WO) ................. PCT/IB2005/002995

(51) Int. Cl.
    G01N 33/53   (2006.01)
(52) U.S. Cl. ..................................... 435/7.1
(58) Field of Classification Search .............. None
    See application file for complete search history.

(56) References Cited

U.S. PATENT DOCUMENTS

| 4,659,659 A | 4/1987 | Dwek et al. |
| 2004/0147033 A1 | 7/2004 | Shriver et al. |
| 2004/0253651 A1 | 12/2004 | Saarinen et al. |
| 2006/0269979 A1 | 11/2006 | Dwek et al. |
| 2006/0270048 A1 | 11/2006 | Dwek et al. |

FOREIGN PATENT DOCUMENTS

| WO | WO 02/08760 A1 | 1/2002 |
| WO | WO 03/016464 A2 | 2/2003 |
| WO | WO 2004/066808 A2 * | 12/2003 |
| WO | WO 2004/019040 A1 * | 3/2004 |
| WO | WO 2004/066808 A2 * | 8/2004 |

OTHER PUBLICATIONS

Tockman et al (Cancer Res., 1992, 52:2711s-2718s).*
Fukuda et al (The Journal of Biological Chemistry, Sep. 1986, 261(27): 12796-12806).*
Kannicht et al (Glycobiology, 1999, 9(9): 897-906).*
Peracaula et al (Glycobiology, 2003, 13(6): 457-470).*
Amano, J. et. al., "Quantitative Conversion of Mucin-Type Sugar chains to Radioactive Oligosaccharides," Methods Enzymol 179: 261-70, 1989.
Amess et al., "Programmed cell death in sympathetic neurons: a study by two-dimensional polyacrylamide gel electrophoresis using computer image analysis," Electrophoresis 16: 1255-1267, 1995.
Anumula et al., "Characterization of carbohydrates using highly fluorescent 2- aminobenzoic acid tag following gel electrophoresis of glycoproteins." Analytical Biochemistry, 275: 236-42, (1999).
Anumula, K. R., "Thematic Review: High-sensitivity and high-resolution methods for glycoprotein analysis." Analytical Biochemistry, 2000, 283: 17-26.
Axford, John S., "Glycosylation and rheumatic disease," Biochimica et Biophysica Acta, Oct. 8, 1999, vol. 1455, No. 2-3, pp. 219-229.
Bigge, J. C., et. al. "Nonselective and efficient fluorescent labeling of glycans using 2-amino benzamide and anthranilic acid," Analytical Biochemistry, 230: 229-38, 1995.
Blass, S., "Novel 68 kDa autoantigen detected by rheumatoid arthritis specific antibodies," Annals of the Rheumatic Diseases, 54:355-360, 1995.
Block et al., "Use of targeted glycoproteomics to identify serum glycoproteins that correlate with liver cancer in woodchucks and humans." Proc Natl Acad Sci U S A, 2005, 102: 779-84.
Brawer MK, "Prostate- specific antigen: current status," CA Cancer J Clin, 49, 264-281, 1999.
Burlingame, A. L., "Characterization of protein glycosylation by mass spectrometry." Curr Opin Biotechnol 7: 4-10, (1996).

(Continued)

Primary Examiner—Sean E Aeder
(74) Attorney, Agent, or Firm—Foley & Lardner LLP

(57) ABSTRACT

One can identify and quantify one or more glycosylation markers of cancer by utilizing quantitative HPLC analysis of glycans which have been released from unpurified glycoproteins. The unpurified glycoproteins can be total glycoproteins or a selection of the total glycoproteins. The identified glycosylation marker can be a native glycan or a digestion product which has been segregated and amplified by exoglycosidase digestions. One can utilize the identified glycosylation marker, for example, for diagnosing and/or monitoring cancer in a subject. One can also use the glycosylation marker to identify glycoprotein biomarkers that carry the glycosylation marker. Such biomarkers can also be used for monitoring and/or diagnosing cancer. The biomarker may also be a subset of glycoforms of a glycoprotein that are separated in trains of spots on 2D gel.

33 Claims, 15 Drawing Sheets

OTHER PUBLICATIONS

Butler, M., et al. "Detailed glycan analysis of serum glycoproteins of patients with congenital disorders of glycosylation indicates the specific defective glycan processing step and provides an insight into pathogenesis." Glycobiology 13: 601-22, 2003.

Caesar et al., "Femtomole oligosaccharide detection using a reducing-end derivative and chemical ionization mass spectrometry," Analytical Biochemistry, 191: 247-52 (1990).

Callewaert et al., "Total serum protein N-glycome profiling on a capillary electrophoresis-microfluidics platform," Electrophoresis, 2004, 25: 3128-31.

Callewaert et al., "Increased fucosylation and reduced branching of serum glycoprotein N-glycans in all known subtypes of congenital disorder of glycosylation I." Glycobiology, 2003, 13: 367-375.

Chan et al., "Alpha-fetoprotein variants in a case of pancreatoblastoma," *Ann Clin Biochem* 37 ( Pt 5): 681-5, 2000.

Ciolczyk-Wierzbicka et al., "The structure of the oligosaccharides of N-cadherin from human melanoma cell lines," Glycoconjugate Journal, 2004, vol. 20, No. 7-8, pp. 483-492.

Costello, C. E., "Bioanalytic applications of mass spectrometry." Curr Opin Biotechnol 10: 22-8, 1999.

Davies et al., "Comparison of separation modes of high-performance liquid chromatography for the analysis of glycoprotein- and proteoglycan-derived oligosaccharides." J Chromatogr A 720: 227-33, 1996.

Despres et. al., "The Sa system: a novel antigen-antibody system specific for rheumatoid arthritis," J Rheumatol 21:1027-33, 1994.

Diamandis E., "Prostate-Specific antigen: Its Usefulness in Clinical Medicine," TEM, 9:310-316, 1998.

Dlamandis, Clin. Lab. News 1996, 22: 235-239.

Duffy, M.J., "CA15.3 and related mucins as circulating markers in breast cancer," Ann. Clin. Biochem., 36, 579-586, 1999.

Edwards et. al., "Efficacy of B-cell-targeted therapy with rituximab in patients with rheumatoid arthritis," N Engl J Med, 350:2572, 2004.

El Rassi, Z., "Recent developments in capillary electrophoresis and capillary electrochromatography of carbohydrate species." Electrophoresis 20: 3134-44, 1999.

Ey et. al. "Isolation of pure $IgG_1$, $IgG_{2a}$ and $IgG_{2b}$ Immunoglobulins from mouse serum using protein A-Sepharose," *Molecular Immunology*, vol. 15, pp. 429, 1978.

Görg et al., "Current two-dimensional electrophoresis technology for proteomics," Proteomics, 4, 3665-3685, 2004.

Görg et al., "Horizontal SDS-PAGE for IGP-Dalt," Methods Mol. Biol, 112, 235-244, 1999.

Guile et al., "Analytical and preparative separation of anionic oligosaccharides by weak anion-exchange high-performance liquid chromatography on an inert polymer column." Analytical Biochemistry, 1994, 222: 231-5.

Guile et al., "Identification of highly fucosylated N-linked oligosaccharides from the human parotid gland," European Journal of Biochemistry, 1998, 258: 623-656.

Guile et. al., "A rapid high-resolution high-performance liquid chromatographic method for separating glycan mixtures and analyzing oligosaccharide profiles," Anal. Biochem. 240: 210-26, 1996.

Hardy et al., "High-pH anion-exchange chromatography of glycoprotein-derived carbohydrates," Methods Enzymol, 230: 208-25, 1994.

Harvey et al., "Proteomic analysis of glycosylation: structural determination of N- and O-linked glycans by mass spectrometry," Expert Review of Proteomics 2005, Apr. 1, 2005, vol. 2, No. 1, pp. 87-101.

Harvey, D. J., "Matrix-assisted laser desorption/ionization mass spectrometry of carbohydrates," Mass Spectrom Rev, 1999, 18: 349-450.

Harvey, D. J., "Electrospray mass spectrometry and fragmentation of N-linked carbohydrates derivatized at the reducing terminus," J Am Soc Mass Spectrum, 2000, 11: 900-915.

Harvey, DJ, "Fragmentation of negative ions from carbohydrates: Part 1; Use of nitrate and other anionic adducts for the production of negative ion electrospray spectra from N-linked carbohydrates," J. Am. Soc. Mass Spectrum., 2005, 16, 622-630.

Harvey, DJ, "Fragmentation of negative ions from carbohydrates: Part 2, Fragmentation of high-mannose N-linked glycans," J. Am. Soc. Mass Spectrom., 2005, 16, 631-646.

Harvey, DJ, "Fragmentation of negative ions from carbohydrates: Part 3, Fragmentation of hybrid and complex N-linked glycans," J. Am. Soc. Mass Spectrom., 2005, 16, 647-659.

Hassfeld et al., "Demonstration of a new antinuclear antibody (anti-RA33) that is highly specific for rheumatoid arthritis," Arthritis Rheum, 32:1515-1520, 1989.

Huang et al., "Microscale nonreductive release of O-linked glycans for subsequent analysis through MALDI mass spectrometry and capillary electrophoresis." Analytical Chemistry, 2001, 73: 6063-6069.

Jackson et al., "The use of polyacrylamide gel electrophoresis for the analysis of acidic glycans labeled with the fluorophore 2-aminoacridone," Electrophoresis, 15: 896-902, 1994.

Johnson et al., "Structures of disease-specific serum alpha-fetoprotein isoforms " Br J Cancer 83(10): 1330-7, 2000.

Kassahn et. al., "Few human autoimmune sera detect GPI," Nat Immunol 3:411-412, 2002.

Keesee et. al., "Utilization of Nuclear Matrix Proteins for Cancer Diagnosis," Crit. Rev. Eukaryotic Gene Expr, 1996, 6(2&3): 189-214.

Klee et al., "MUC1 gene-derived glycoprotein assays for monitoring breast cancer (CA 15-3), CA 27.29, BR): Are They Measuring the Same Antigen?", Arch. Pathol. Lab. Med., 128, 1131-1135, 2004.

Kozak et. al., "Identification of biomarkers for ovarian cancer using strong anion-exchange ProteinChips: Potential use in diagnosis and prognosis," PNAS, 100:12343-12348, 2003.

Kuster et al., "Sequencing of N-linked oligosaccharides directly from protein gels: in-gel deglycosylation followed by matrix-assisted laser desorption/ionization mass spectrometry and normal-phase high-performance liquid chromatography." Anal-Biochem, 1997, 250: 82-101.

Laemmli, UK, "Cleavage of structural proteins during the assembly of the head of bacteriophage T4," Nature, 227, 680-685, 1970.

Lillemoe et al., "Pancreatic cancer: state-of-the art care," Cancer J. Clin., 50, 241-268, 2000.

Mattu et al., "O-glycan analysis of natural human neutrophil gelatinase B using a combination of normal phase-HPLC and online tandem mass spectrometry: implications for the domain organization of the enzyme," Biochemistry 39: 15695-704, 2000.

Mattu et al., "The glycosylation and structure of human serum IgA1, Fab, and Fc regions and the role of N-glycosylation on Fc alpha receptor interactions," Journal of Biological Chemistry 273: 2260-72, 1998.

Mazor et al., "Humanization and epitope mapping of the H23 anti-MUC1 monoclonal antibody reveals a dual epitope specificity," Mol Immunol., Jan. 2005, 42(1):55-69.

Mor et al., "Serum protein markers for early detection of ovarian cancer," PNAS, 102:7677-7682, 2005.

Nienhuis et al., "A new serum factor in patients with rheumatoid arthritis. The antiperinuclear factor," Annals of Rheumatic Disease, 23:302, 1964.

Papac et. al., "A high-throughput microscale method to release N-linked oligosaccharides from glycoproteins for matrix-assisted laser desorption/ionization time-of-flight mass spectrometric analysis," Glycobiology, 8: 445-54, 1998.

Parekh et al., "A comparative analysis of disease-associated changes in the galactosylation of serum IgG," J. Autoimmunity, 2:101-114, 1989.

Parekh et al., "Galactosylation of IgG associated oligosaccharides: Reduction in patients with adult and juvenile onset rheumatoid arthritis and relation to disease activity," Lancet, pp. 966-969, Apr. 1988.

Parekh et al., "N-Glycosylation and in vitro Enzymatic Activity of Human Recombinant Tissue Plasminogen Activator Expressed in Chinese Hamster Ovary Cells and a Murine Cell line" Biochemistry, 1989, 28, 7670-7679.

Parekh et al., 3rd Jenner International Immunoglycobiology Meeting Abstract, *Glycoconjugate Journal* (1994) 1, 3 195-227.

Parekh et. al. "Association of Rheumatoid Arthritis and Primary Osteoarthritis with Changes in the Glycosylation Pattern of Total Serum IgG," Nature, 316, pp. 452-457, 1985.

Peracaula et al., "Altered glycosylation pattern allowes the distinction between prostate-specific antigen (PSA) from normal and tumor origins." Glycobiology, 13: 457-70, 2003.

Peracaula et al., "Glycosylation of human pancreatic ribonuclease: differences between normal and tumor states," Glycoblology, Apr. 1, 2003, vol. 13, No. 4, pp. 227-244.

Perkins et al., "Serum tumor markers," American Family Physician, 68, 1075-1082, 2003.

Reinhold et al., "Carbohydrate sequence analysis by electrospray ionization-mass spectrometry," Methods Enzymol, 271: 377-402, 1996.

Rønningen et. al., "Rheumatoid arthritis may be primarily associated with HLA-DR4 molecules sharing a particular sequence at residues 67-74," Tissue Antigens 36:235-240, 1990.

Rooney et.al., "The immunohistologic features of synovitis, disease activity and in vitro IgM rheumatoid factor synthesis by blood mononuclear cells in rheumatoid arthritis," Journal of Rheumatology, 16:459-467, 1989.

Royle et. al., "An analytical and structural database provides a strategy for sequencing O-glycans from microgram quantities of glycoproteins," Anal. Biochem. 304: 70-90, 2002.

Sanchez et al., "Improved and simplified in-gel sample application using reswelling of dry immobilized pH gradients," Electrophoresis, 18: 324-327, 1997.

Schaller et. al., "Autoantibodies to GPI in rheumatoid arthritis: linkage between an animal model and human disease," Nat Immunol, 2:746-753, 2001.

Schubert et. al, "Autoantibodies to GPI and creatine kinase in RA," Nat Immunol, 3:411; discussion 412, 2002.

Smith et. al., "Measurement of protein using bicinchoninic acid," Analytical Biochemistry, 150: 76-85, 1985.

Stein et. al., "Prognostic markers in bladder cancer: a contemporary review of the litearture," J. Urol, 1998, 160(3, pt 1):645-659.

Taylor-Papadimitriou et al., "MUC1 and cancer," Biochem. Biophys. Acta., 1455:301-313, 1999.

Townsend et al., "High-performance anion-exchange chromatography of oligosaccharides using pellicular resins and pulsed amperometric detection," Analytical Biochemistry, 174: 459-70, 1988.

Van Boekel et. al., "Autoantibody systems in rheumatoid arthritis: specificity, sensitivity and diagnostic value," Arthritis Res, 4:87-93, 2002.

Van Boxel et al., "Predominantly T-cell infiltrate in rheumatoid synovial membranes," New England Journal of Medicine, 293:517-520, 1975.

Watkins et al., "Detection of early-stage cancer by serum protein analysis," American Laboratory. Jun. 2001, 32-36.

Watson et al., "Sugar Printing Rheumatic Diseases: A Potential Method for Disease Differentiation Using Immunoglobulin G Oligosaccharides," Arthritis and Rheumatism, 42(8):1682-1690, 1999.

Wittwer et al., "Effects of N-Glycosylation on in vitro Activity of Bowes Melanoma and Human Colon Fibroblast Derived Tissue Plasminogen Activator," Biochemistry, 1989, 28, 7662-7669.

Wordsworth et al., "HLA-DR4 subtype frequencies in rheumatoid arthritis indicate that DRB1 is the major susceptibility locus within the HLA class II region," Proceedings of the National Academy of Sciences of the United States of America, 86:10049-10053, 1989.

Yeo et al., "Epidemiology and Risk Factors," Current Problems in Cancer 26(4):176-275, 2002.

Young et. al, "Anti-keratin antibodies in rheumatoid arthritis", Br Med J, 2:97-99, 1997.

Office Action mailed Aug. 19, 2009 in U.S. Appl. No. 11/411,231 (US Publication 2006-0269979), 11 pages.

DeGroot et al., "Molecular markers for osteoarthritis: the road ahead," Current Opinion in rheymatology, 2002, 14:585-589.

Lebrilla et al., "The prospects of glycan biomarkers for the diagnosis of diseases," Molecular Biosystems, 2009, 5:17-20.

Scofield, R.H., "Autoantibodies as predictors of disease," The Lancet, 2004, 363:1544-1546.

Villalta et al., "The laboratory approach to the diagnosis of autoimmune diseases: Is it time to change?" Autoimmunity Reviews, 2007, 6:359-365.

Wollheim et al., "Markers of disease in rheumatoid arthritis," Current Opinion in Rheumatology, 2000, 12:200-204.

Non-final Office Action mailed Dec. 4, 2009 in U.S. Appl. No. 11/411,232 (US Publication No. 2006-0270048), 22 pages.

Final Office Action mailed Mar. 30, 2010, in U.S. Appl. No. 11/411,231.

Final Office Action mailed May 13, 2010, in U.S. Appl. No. 11/411,232.

* cited by examiner

Exoglycosidase digestion of whole serum glycans highlights differences in breast cancer glycosylation

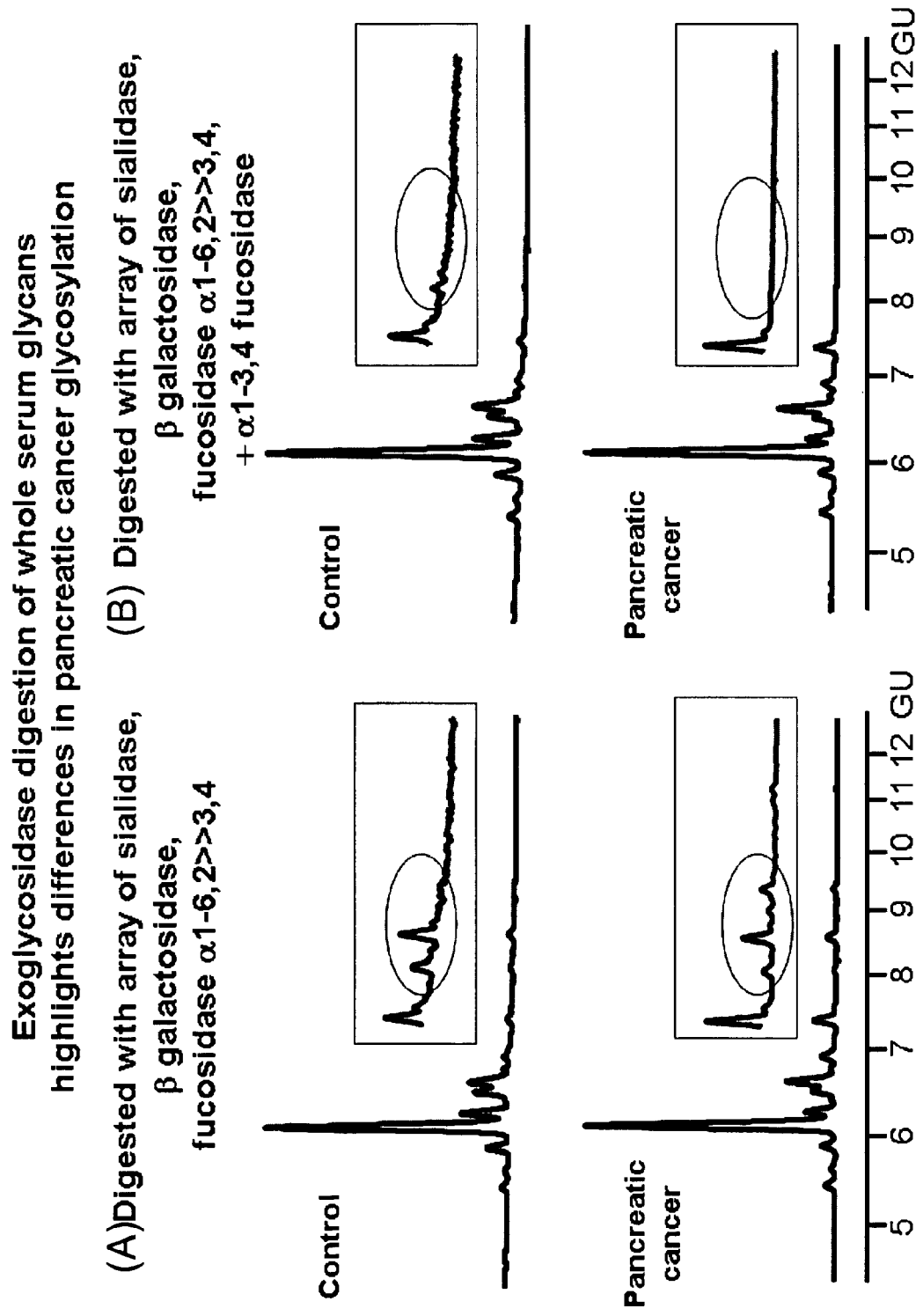
FIGURE 5 (A)-(B)
Exoglycosidase digestion of whole serum glycans highlights differences in pancreatic cancer glycosylation
(A) Digested with array of sialidase, β galactosidase, fucosidase α1-6,2>>3,4
(B) Digested with array of sialidase, β galactosidase, fucosidase α1-6,2>>3,4, + α1-3,4 fucosidase

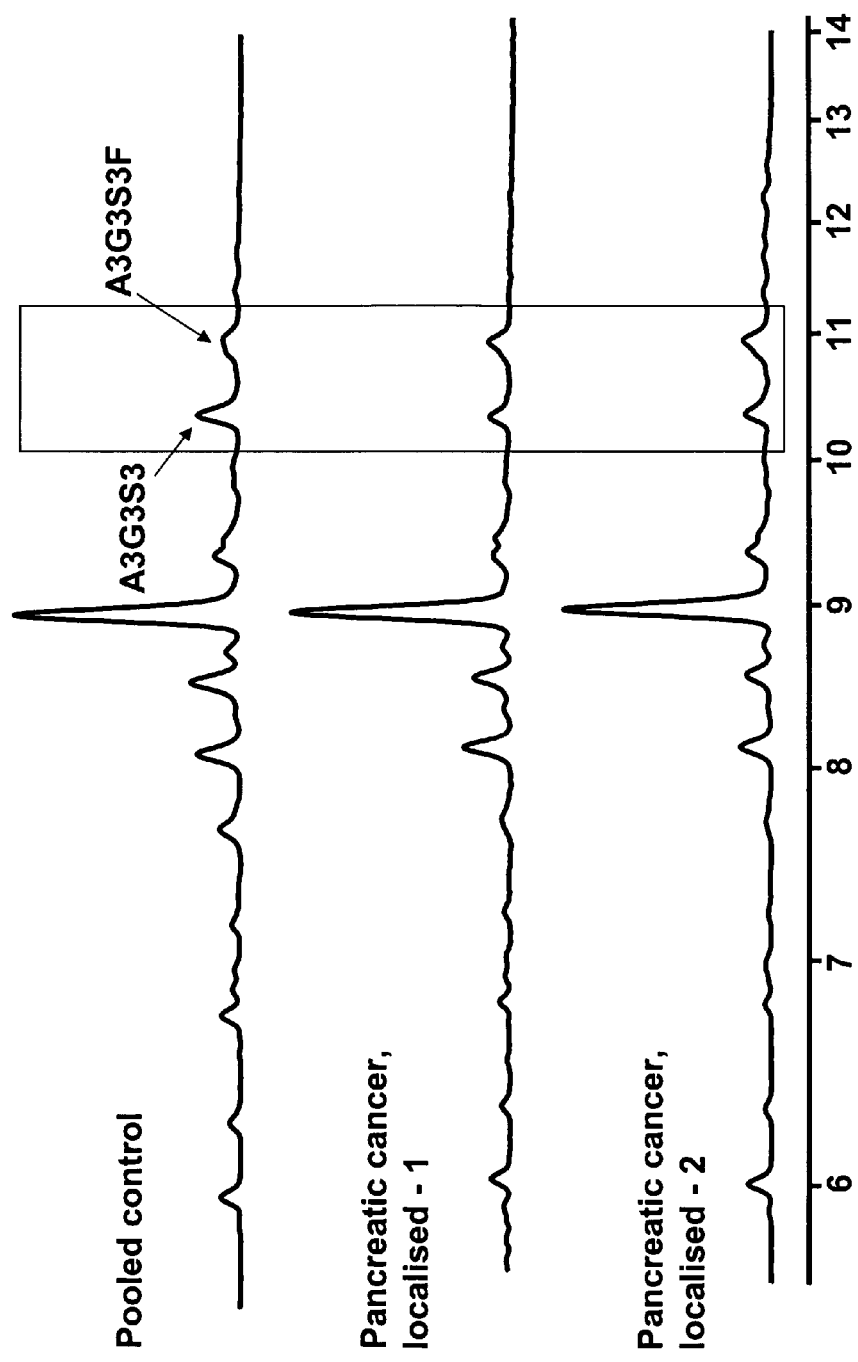

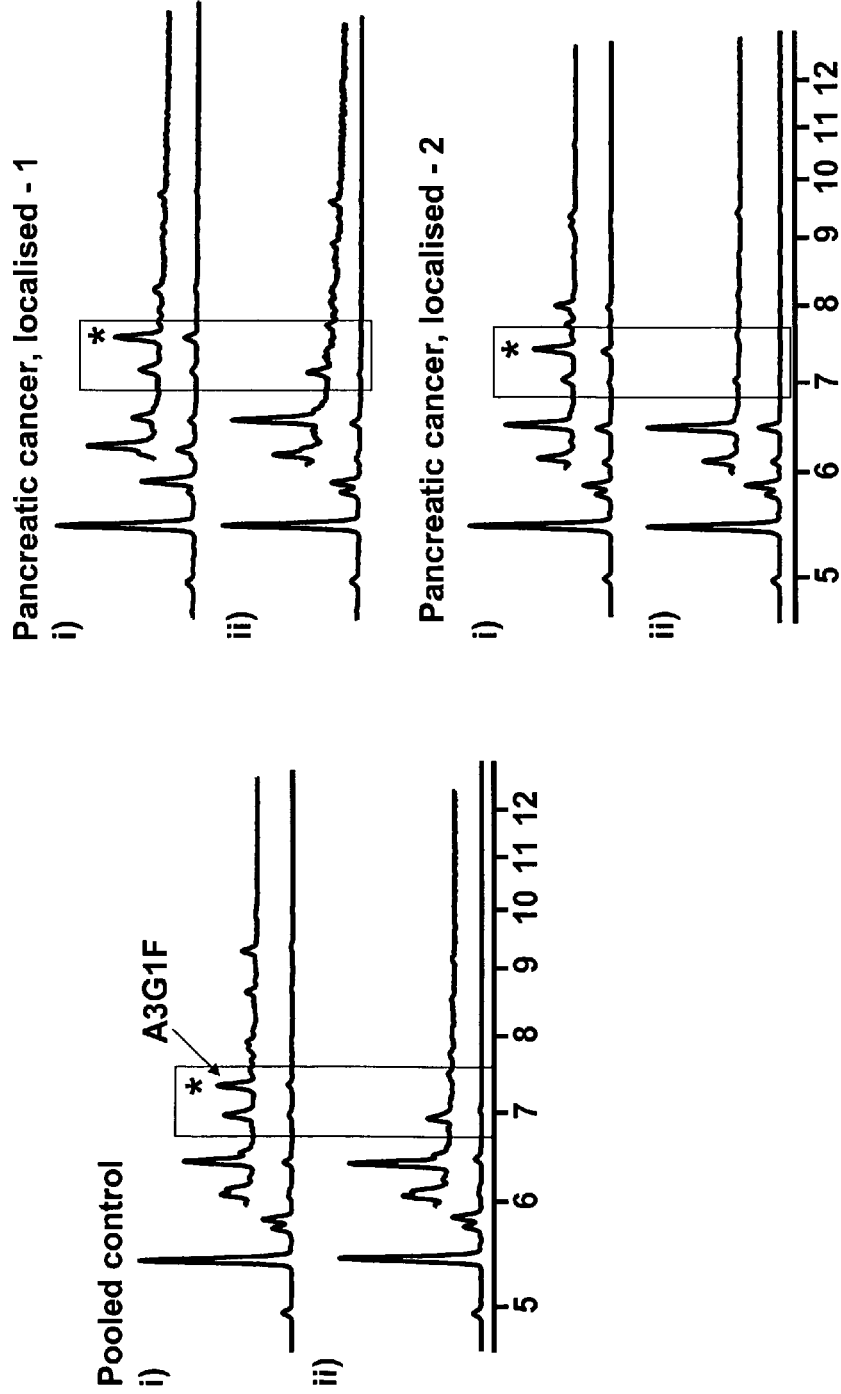

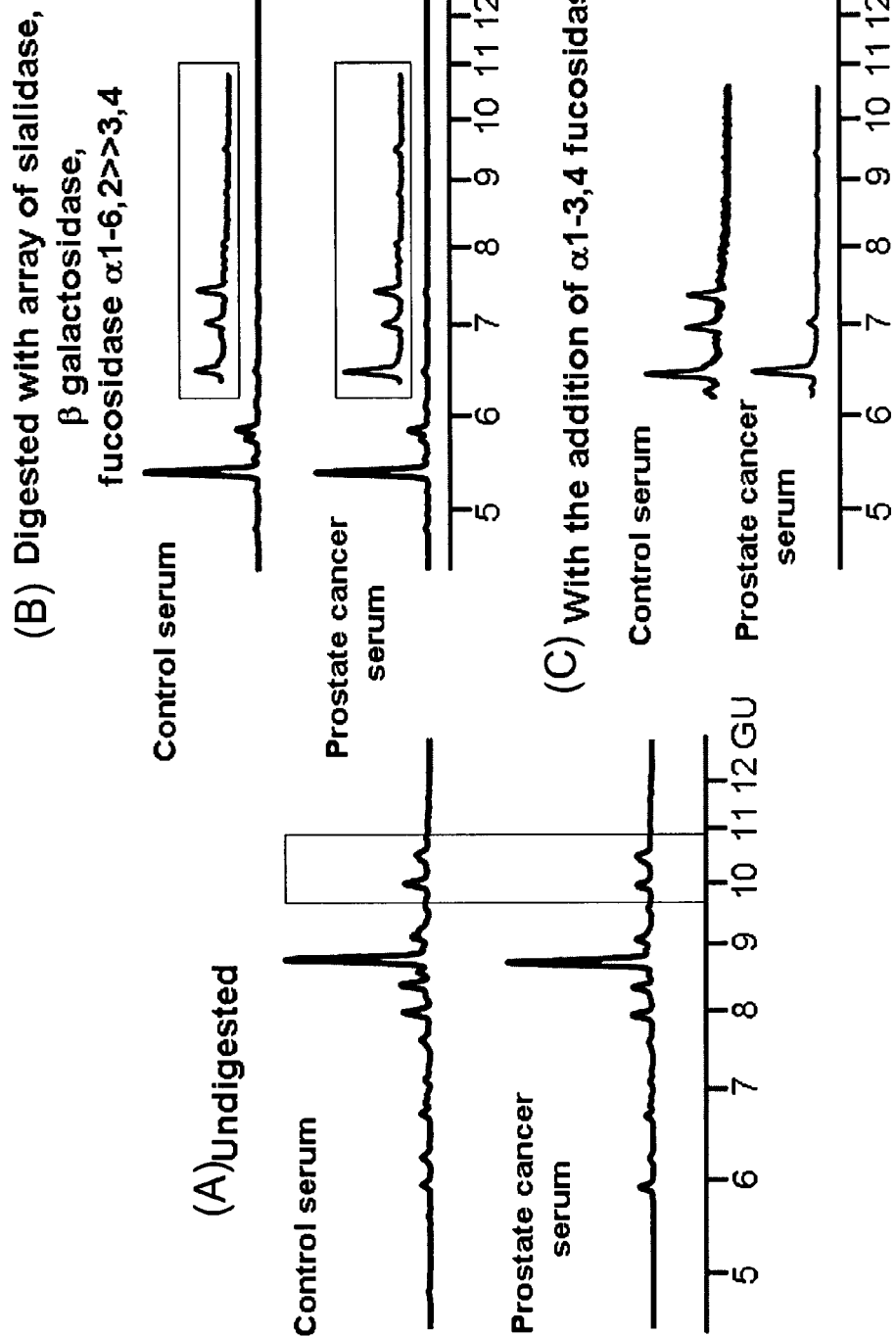
FIGURE 6(A)-(C)
Exoglycosidase digestion of whole serum glycans highlights differences in prostate cancer glycosylation

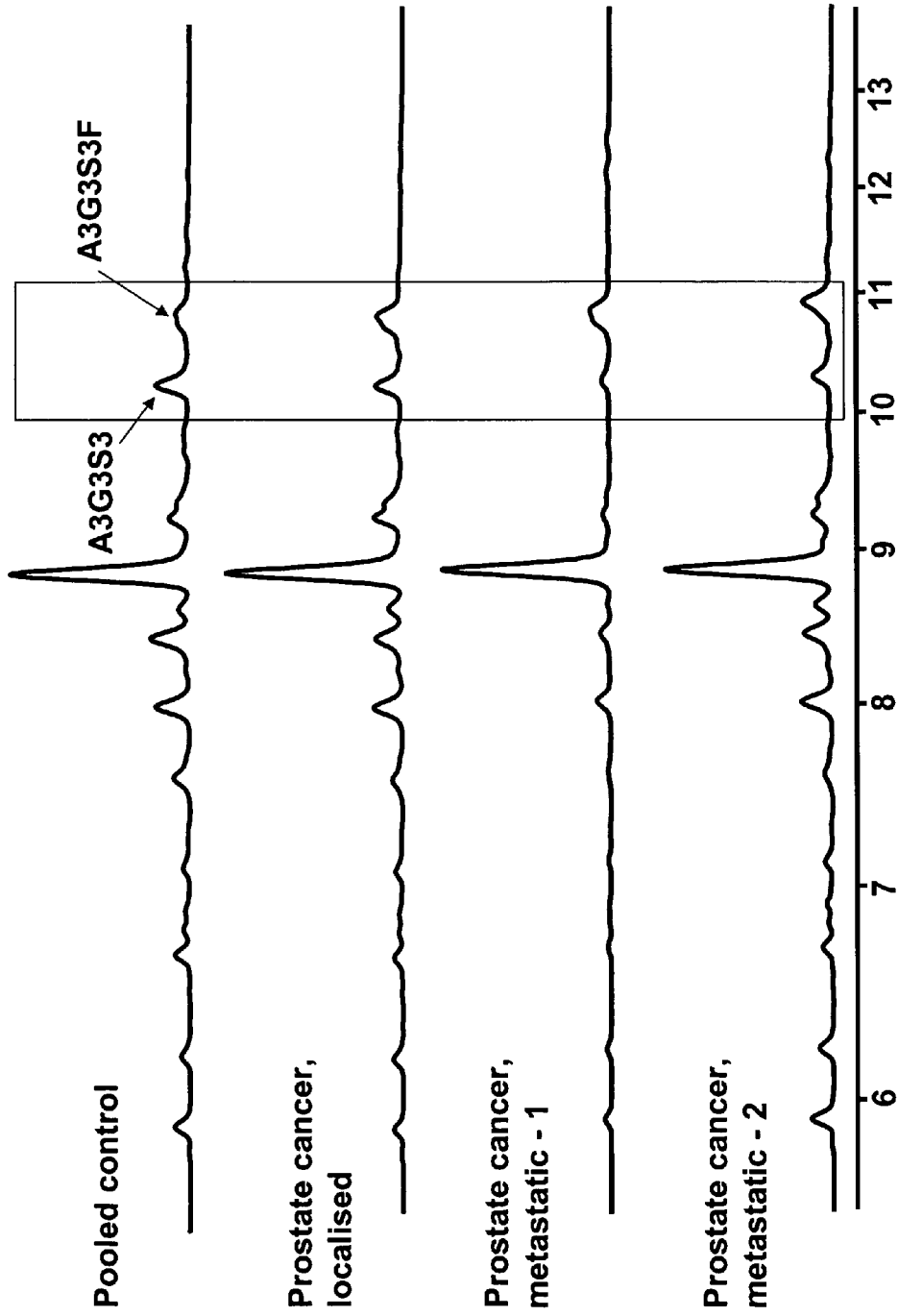

Exoglycosidase digestions of whole serum glycans highlights differences in prostate cancer glycosylation Digested with array of i) sialidase, β galactosidase, fucosidase α1-6,2>>3,4
ii) with the addition of α1-3,4 fucosidase

FIGURE 7(A)-(C)
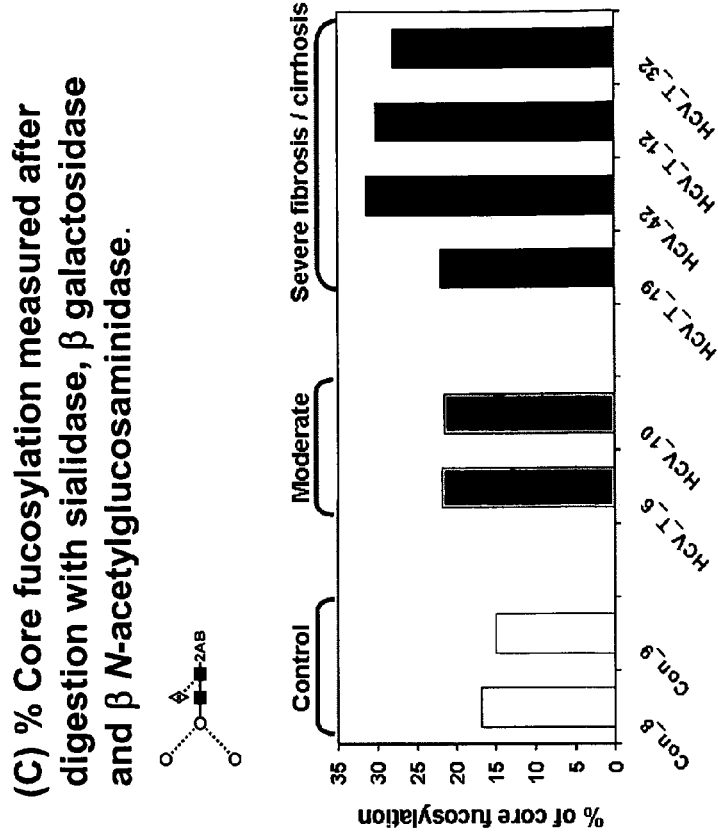
(C) % Core fucosylation measured after digestion with sialidase, β galactosidase and β N-acetylglucosaminidase.
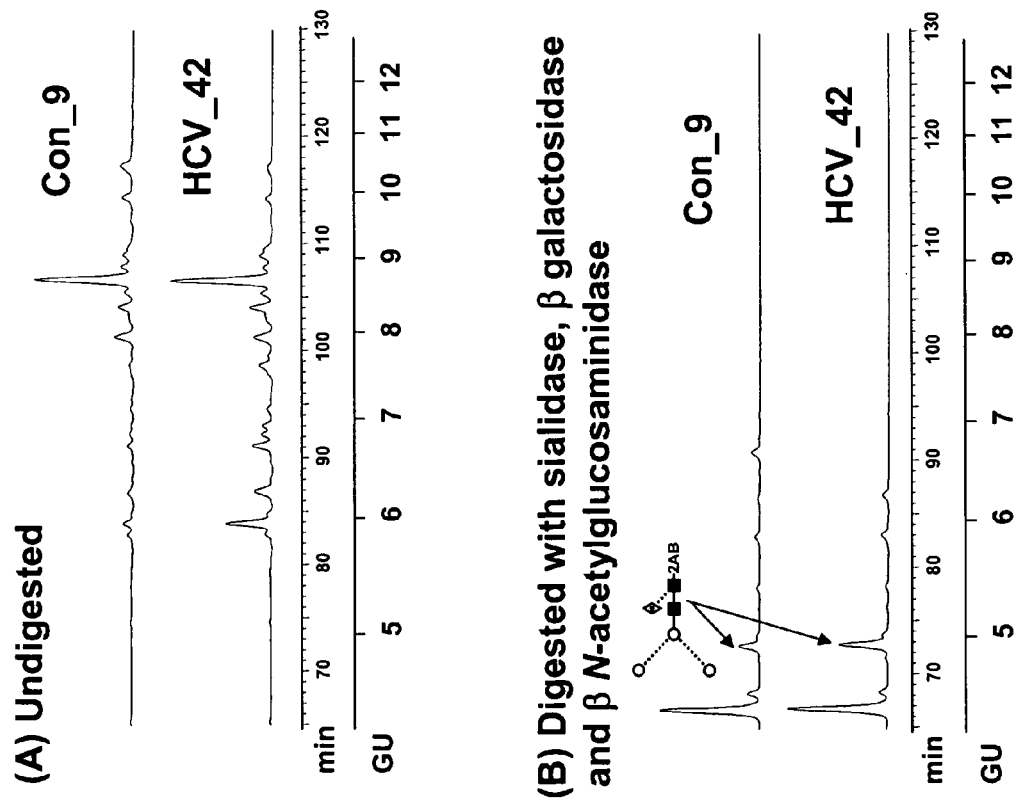
(A) Undigested
(B) Digested with sialidase, β galactosidase and β N-acetylglucosaminidase

FIGURE 8(A)-(C)
Exoglycosidase digestion of whole serum glycans highlights differences in ovarian cancer glycosylation
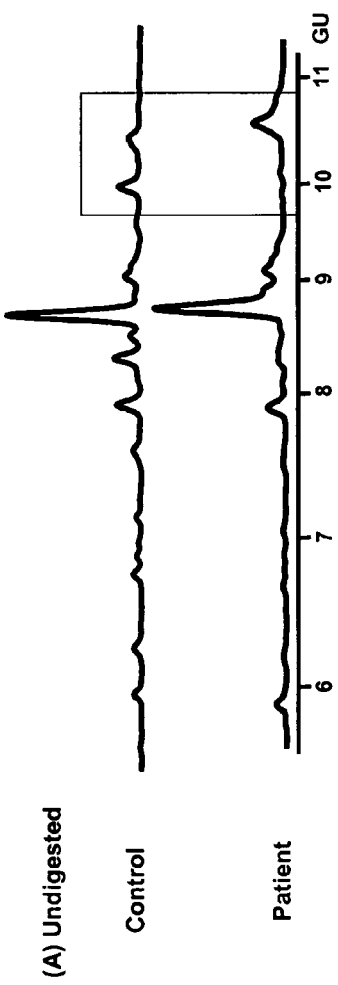
(A) Undigested
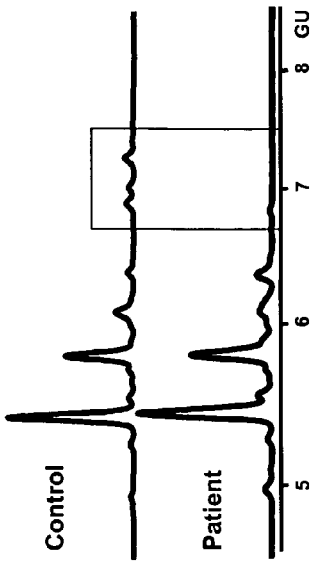
(B) Digested with sialidase, β galactosidase α1-2
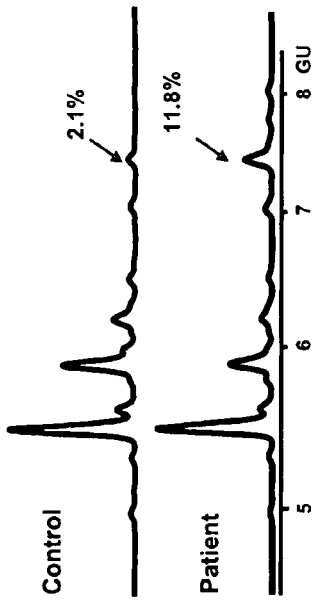
(C) Digested with sialidase, β1-4 galactosidase and fucosidase α1-3/4

Glycosylation analysis of train of haptoglobin β-chain 2D gel spots

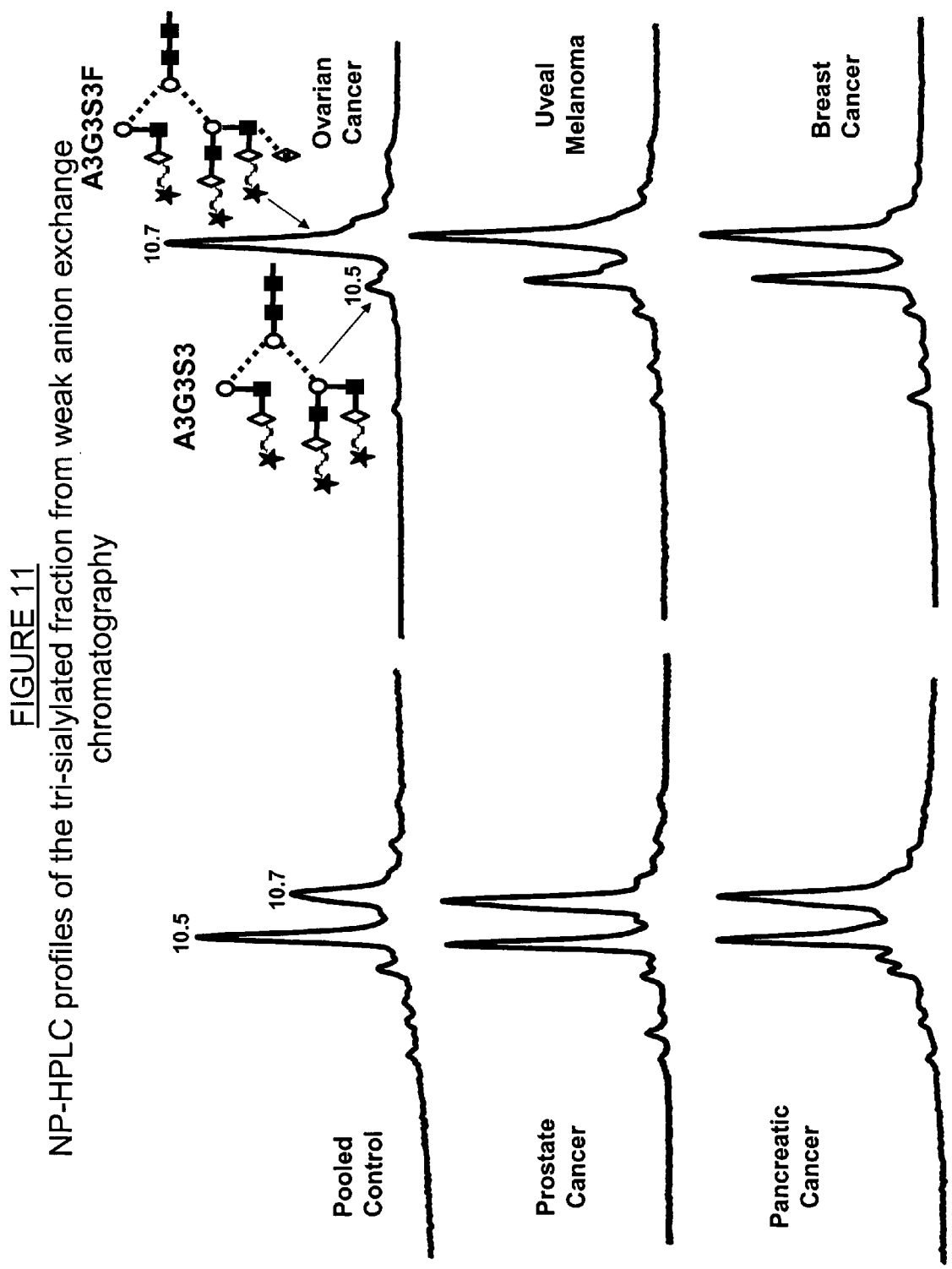

GLYCOSYLATION MARKERS FOR CANCER DIAGNOSING AND MONITORING

PRIORITY CLAIMS

The present application claims priority to U.S. provisional patent applications Nos. 60/674,724 to Dwek et. al. filed Apr. 26, 2005 and 60/674,723 to Dwek et. al. filed Apr. 26, 2005, which are both incorporated herein by reference in their entirety. The present application also claims priority to PCT applications Nos. PCT/IB2005/002995 to Dwek et. al. filed Jun. 24, 2005 and PCT/IB2005/002531 to Dwek et. al. filed Jun. 24, 2005, which are both incorporated herein by reference in their entirety.

FIELD

The present invention relates generally to methods of diagnosing and monitoring cancer and, in particular, to methods of diagnosing and monitoring cancer based on detailed glycosylation analysis.

BACKGROUND

Presymptomatic screening to detect early-stage cancer reduces cancer-related mortality and treatment-related morbidity. Although many cancers can be treated and cured if they are diagnosed while tumors are still localized, most cancers are not detected until after they have invaded the surrounding tissue or metastasized to distant sites. For example, only 50% of breast cancers, 56% of prostate cancers and 35% of colorectal cancers are localized at the time of diagnosis, see Watkins, B., Szaro, R., Ball, S., Knubovets, T., Briggman, J., Hlavaty, J. J., Kusinitz, F., Stieg, A., and Wu, Y. (2001) Detection of early-stage cancer by serum protein analysis. American Laboratory. June, 32-36. incorporated herein by reference in its entirety. The situation is much worse for other, less treatable types of cancer. For example, about 80% of pancreatic cancers are already metastatic at the time of diagnosis which results in 1-year survival rate after diagnosis of about 19% and 5-year survival rate of about 4%. Similar 5-year survival rates (<5%) were reported for hepatocellular carcinoma. As therapeutic options for cancer treatment increase, early detection of cancer becomes important for improving prognosis.

In recent years, several serum protein markers have been developed for certain types of cancer. For example, prostate specific antigen (PSA), a glycoprotein secreted by prostate cells that is found in serum in prostate pathologies, is currently used as a tumor marker for prostate cancer. Other protein markers for cancer diagnostics and monitoring are alpha-fetoprotein for hepatocellular carcinoma and testicular cancer, NMP22 for bladder cancer, catecholamines for neuroblastoma, immunoglobulins for multiple myeloma, carcinoembryonic antigen (CEA) for colorectal cancer, HER-2, CA 15-3 and CA 27-29 for breast cancer, CA 125 for ovarian cancer, CA19-9 for pancreatic cancer, see Keesee et. al. Crit. Rev. Eukaryotic Gene Expr, 1996, 6(2&3): 189-214; Diamandis, Clin. Lab. News 1996, 22: 235-239, Stein et. al. J. Urol 1998, 160(3, pt 1):645-659. Although the development of the serum markers facilitated the clinical management of certain types of cancer, the assays of these biomarkers are neither sensitive nor specific enough for use as the sole screening method for cancer diagnostics. Thus, it is highly desirable to develop new cancer-related biomarkers that will be more sensitive and more specific to detect recurrence and metastases at the earliest stages for both diagnosing and monitoring cancer progression.

Methods of developing new cancer-related biomarkers were suggested based on the difference in glycosylation in glycoproteins from cancer patients and healthy controls. For example, Block et. al. was comparing glycosylation profiles in immunoglobulin G (IgG) depleted sera from hepatitis B virus infected subjects (humans and woodchucks) with hepatocellular carcinoma and from respective healthy controls to identify particular glycoproteins with glycosylation changes as cancer-related biomarkers, see Block, T. M., Comunale, M. A., Lowman, M., Steel, L. F., Romano, P. R., Fimmel, C., Tennant, B. C., London, W. T., Evans, A. A., Blumberg, B. S., Dwek, R. A., Mattu, T. S. and Mehta, A. S. (2005). "Use of targeted glycoproteomics to identify serum glycoproteins that correlate with liver cancer in woodchucks and humans." Proc Natl Acad Sci USA 102: 779-84, incorporated herein by reference. Particular differences in glycosylation profiles of purified glycoproteins between diseased patients and healthy controls can serve themselves as markers of the disease. For example, a clear correlation between rheumatoid arthritis and the percentage of the galactosylation on N-glycans released from purified immunoglobulin G (IgG) has been established in Parekh et al., see "Association of Rheumatoid Arthritis and Primary Osteoarthritis with Changes in the Glycosylation Pattern of Total Serum IgG," Nature, 316, pp. 452-457, 1985, incorporated herein by reference in its entirety. Alterations in glycosylation profiles of purified glycoproteins were also reported for certain types of cancer. For example, glycosylation was found to be different for glycans released from purified PSA from seminal plasma and from purified PSA secreted by the tumor prostate cell line LNCaP, see Peracaula R, Tabarés G, Royle L, Harvey D J, Dwek R A, Rudd, P M, de Llorens R. (2003). Altered glycosylation pattern allows the distinction between Prostate Specific Antigen (PSA) from normal and tumor origins, Glycobiology, 13, 457-470, incorporated herein by reference in its entirety. Completely different glycosylation profiles were found for pancreatic ribonuclease (RNase 1) isolated from healthy pancreas and from pancreatic adenocarcinoma tumor cells (Capan-1 and MDA-Panc-3), see Peracaula R, Royle L, Tabarés G, Mallorquí-Fernández G, Barrabés S, Harvey D, Dwek R A, Rudd, P M, de Llorens R. (2003) "Glycosylation of human pancreatic ribonuclease: differences between normal and tumour states", Glycobiology, 13, 227-244, incorporated herein by reference in its entirety. Thus, glycosylation analysis can be a powerful tool for identifying cancer-related biomarkers, however, currently used methods involve purifying glycoproteins, a step which can be time consuming and which can require a large amount of sample material from patients. Accordingly, it is highly desirable to develop methods for identifying cancer-related glycosylation markers and related methods for diagnosing and monitoring cancer that would not comprise purifying glycoproteins. Performing glycosylation analysis on whole, i.e. not depleted and not purified, samples can be particularly beneficial for cancer diagnostics and monitoring. Although differences in the glycosylation profile can be associated with the presence in samples of cancer patients of glycoproteins specifically associated with cancer, such as alpha-fetoprotein (see e.g. Johnson, P. J., T. C. Poon, et al. (2000). "Structures of disease-specific serum alpha-fetoprotein isoforms." Br J Cancer 83(10): 1330-7; and Chan, M. H., M. M. Shing, et al. (2000). "Alpha-fetoprotein variants in a case of pancreatoblastoma." Ann Clin Biochem 37 (Pt 5): 681-5), many other tumor glycoproteins, i.e. glycoproteins that are not specific inflammatory markers of cancer, can be expected to carry altered glycosylation because glycosylation pathways are usually disturbed in tumor cells, see e.g. "Effects of N-Glycosylation on in vitro Activity of Bowes Melanoma and Human Colon Fibroblast Derived Tissue Plasminogen Activator" Art Wittwer, Susan Howard, Linda S. Carr, Nikos K. Harakas, Joseph Feder Raj B. Parekh, Pauline M. Rudd, Raymond A. Dwek and Thomas W. Rademacher Biochemistry, 1989, 28, 7662-7669; "N-Glycosylation and in vitro Enzymatic Activity of Human Recombinant Tissue Plasminogen Activator Expressed in Chinese Hamster Ovary Cells and a Murine Cell line" Raj B. Parekh, Raymond A. Dwek, Pauline M. Rudd, Jerry R. Thomas, T. W. Rademacher, T. Warren, T. C. Wun, B. Herbert, B. Reitz, M. Palmier, T. Ramabhadran and D. C. Teimeir Biochemistry 1989, 28, 7670-7679, both incorporated herein in their entirety. Based on the above, performing detailed glycosylation analysis on samples of whole body fluid or body tissue, without isolating or purifying specific glycoproteins, can be expected to identify glycosylation markers of cancer amplified compared with glycosylation analysis of purified glycoproteins.

SUMMARY

According to one embodiment, one can identify and/or quantify one or more glycosylation of cancer by a method comprising (A) obtaining a sample from a subject diagnosed with the cancer; (B) releasing glycans of unpurified glycoproteins from the sample; (C) measuring a glycosylation profile of the glycans by quantitative high performance liquid chromatography alone or in combination with mass spectrometry; and (D) comparing the glycosylation profile with a control profile to determine the one or more glycosylation markers of the cancer.

According to another embodiment, one can diagnose and/or monitor cancer in a subject by a method comprising (A) obtaining a sample from the subject; (B) releasing glycans of unpurified glycoproteins from the sample; (C) measuring a glycoprofile of the glycans by quantitative high performance liquid chromatography; and (D) comparing the glycoprofile with a control profile to determine a level of a glycosylation marker of the cancer.

According to yet another embodiment, one can identify and/or quantify one or more biomarkers of cancer by a method comprising (A) obtaining a sample from a subject diagnosed with cancer; (B) separating proteins of the sample into a plurality of spots using 2 dimensional electrophoresis, wherein each spot of the plurality corresponds to one or more glycoforms of the proteins; (C) releasing unmodified glycans from one or more spots of said plurality; and (D) measuring a glycoprofile of the glycans using quantitative high performance liquid chromatography, mass spectrometry or a combination thereof for an altered level of one or more glycosylation markers of the cancer.

BRIEF DESCRIPTION OF THE DRAWINGS

FIG. 5(A)-(D) illustrate determination of a glycosylation marker for pancreatic cancer.

FIG. 7 (A)-(C) illustrate determination of a glycosylation marker for hepatocellular carcinoma in hepatitis C virus (HCV) infected patients.

FIG. 8 (A)-(C) illustrates determination of a glycosylation marker for ovarian cancer.

FIG. 9 shows 2-dimensional electrophoresis of serum highlighting the train of spots containing haptoglobin β-chain.

FIG. 11 shows NP-HPLC profiles obtained from the tri-sialylated fraction only collected by ion exchange chromatography.

DETAILED DESCRIPTION

Figure 1:
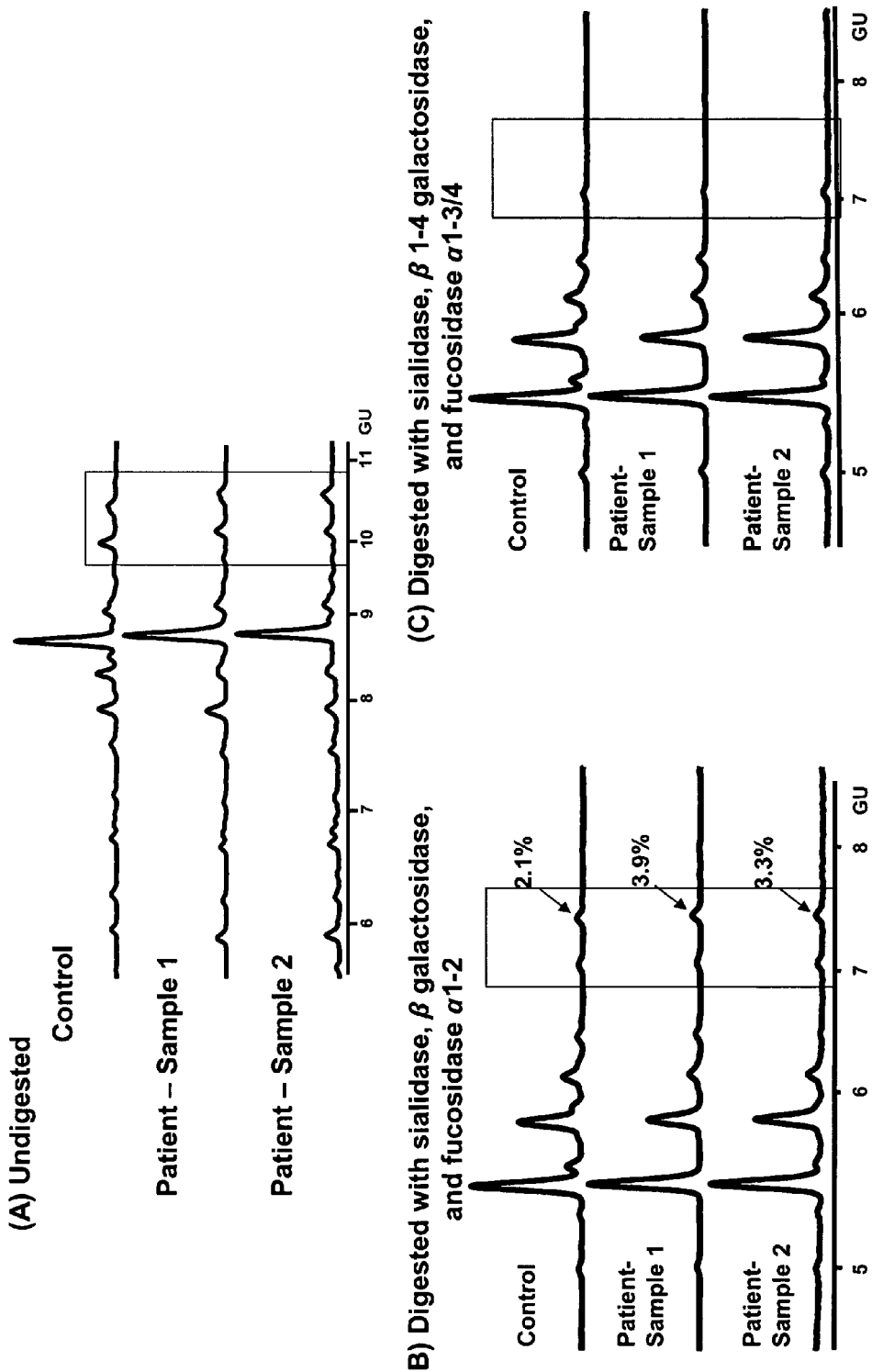
FIG. 1(A)-(C) illustrate determination of a glycosylation marker for breast cancer.

The present invention relates to methods of diagnosing and monitoring cancer and, in particular, to methods of diagnosing and monitoring cancer based on detailed glycosylation analysis.

This application incorporates by reference in their entirety U.S. provisional patent application No. 60/674,724 "An automated glycofingerprinting strategy" to Dwek et. al. filed Apr. 26, 2005 and U.S. provisional patent application No. 60/674, 722 "High Throughput Glycan Analysis for Diagnosing and Monitoring Rheumatoid Arthritis and Other Autoimmune Diseases" to Dwek et. al. filed Apr. 26, 2005.

Unless otherwise specified, "a" or "an" means "one or more".

"Glycoprotein" designates an amino acid sequence and one or more oligosaccharide (glycan) structures associated with the amino acid sequence.

Glycoprotein can have one or more glycoforms. Each of the glycoforms of the particular glycoprotein has the same amino acid sequence, however, glycan structures associated with distinct glycoforms differ by at least one glycan.

"Glycoprofile" or "glycosylation profile" means a presentation of glycan structures (oligosaccharides) present in a pool of glycans. A glycoprofile can be presented, for example, as a plurality of peaks each corresponding to one or more glycan structures present in a pool of glycans.

"Glycosylation marker" means a particular difference in glycosylation between a sample of a subject diagnosed with cancer or cancer condition and a sample from healthy control.

"Control profile" means a glycosylation profile from a sample not affected by cancer. The control sample can originate from a single individual or be a sample pooled from more than one individuals.

The term "subject" means an animal, more preferably a mammal, and most preferably a human.

The high throuput format can mean a standard multiwell format such as 48 well plate or 96 well plate.

The present application incorporates in their entirety U.S. applications "Automated Strategy for Identifying Physiological Glycosylation Marker(s)" to Dwek et. al. filed on Apr. 26, 2006, and U.S. application "High Throughput Glycan Analysis for Diagnosing and Monitoring Rheumatoid Arthritis and Other Autoimmune Diseases" to Dwek et. al. filed Apr. 26, 2006.

The inventors recognized that, in cancer tumor cells, glycosylation can be altered not for one or a few, but for many glycoproteins and, therefore, performing detailed glycosylation analysis on samples of whole body fluid or body tissue, without isolating or purifying specific glycoproteins, will identify glycosylation markers of cancer amplified compared with glycosylation analysis of isolated glycoproteins. The inventors also realized that treating glycans of total glycoproteins with one or more exoglycosidase enzymes could allow the glycosylation markers of cancer to be segregated by shifting glycan structures that do not carry the glycosylation markers from the measured region of the glycoprofile. Furthermore, the inventors recognized that the glycosylation markers could be present on more than one glycan structure in the total glycan pool. Therefore, treating glycans with one or more exoglycosidase enzymes can also amplify the glycosylation markers by digesting away one or more monosaccharides that are attached to some of the marker oligosaccharides but are not an essential feature of the marker. Accordingly, methods for determining one or more glycosylation markers of cancer and related methods for diagnosing and monitoring cancer are provided.

According to one embodiment, one can identify and/or quantify one or more glycosylation markers of cancer in a sample of a subject diagnosed with cancer by measuring a glycoprofile of glycans that have been released from unpurified glycoproteins of the sample and comparing the glycoprofile with a control profile. The sample of the subject can be any sample that contains glycoproteins. The sample can be a sample of a body tissue or a sample of a body fluid such as whole serum, blood plasma, urine, seminal fluid, seminal plasma, pleural fluid, ascites, nipple aspirate, feces or saliva. Particular type of a body fluid or a tissue can depend on the type of cancer. In some embodiments, a sample can be obtained from tumor cells. In some embodiments, the unpurified glycoproteins can be total glycoproteins in the sample, i.e. all the glycoproteins in the sample without any loss. Yet in some embodiments, the unpurified glycoproteins can be a selection of total glycoproteins. The selection of total glycoproteins is not limited to a single type of glycoprotein but still represents a pool or plurality of different types of glycoproteins.

Preferably, glycans are released in such a way so that they are not modified, i.e. the released glycans are the native glycans of the glycoproteins of the sample. In some embodiments, glycans can be released from unpurified glycoproteins in solution. Yet in some embodiments, glycans can be released from immobilized unpurified glycoproteins. In some embodiments, unpurified glycoproteins can be immobilized in a high throughput format such as a multiwell plate.

In some embodiments, the unpurified glycoproteins can be total glycoproteins from the sample that are immobilized in a non-selective format such as gel block. Yet in some embodiments, the unpurified glycoproteins can be a selection of total glycoproteins immobilized on a protein binding membrane such as a PVDF membrane or in a gel piece such as a gel band or a gel spot.

The measurement of the glycoprofile of the released glycans can be carried out by quantitative HPLC alone or in combination with mass spectrometry. The measured glycoprofile can then be compared with a control glycoprofile to determine one or more glycosylation markers of cancer. Comparing the glycoprofiles can involve comparing peak ratios in the profiles. When more than one glycosylation marker is identified, one can select one or more of the markers that have the highest correlation with one or more parameters of the subject diagnosed with cancer. Such parameters can be diagnosis, age, sex, cancer stage, response to therapy, medical history or any combination thereof.

In some embodiments, comparing the glycoprofile of the subject diagnosed with cancer and the control profile can be carried out following digestion of the glycans with one or more exoglycosidases. The exoglycosidase digestion can be a sequential digestion or a digestion with an array comprising one or more exoglycosidase enzymes. The exoglycosidase digestion can be used to amplify and/or segregate the glycosylation marker of cancer. In some embodiments, the determined glycosylation marker can comprise a native glycan of glycoproteins in the sample. Yet in some embodiments, the glycosylation marker can comprise one or more digested glycans. The identified glycosylation marker of cancer can be used for diagnosing, monitoring and/or prognosticating cancer in a subject by measuring a glycoprofile of glycans that have been released from unpurified glycoproteins from a sample of the subject to determine a level of the glycosylation marker in the subject. Measuring of the glycoprofile and determining the level of the glycosylation marker can be carried out by any suitable, i.e. not necessarily by the technique used to determine the glycosylation marker. Example of such alternative techniques can be capillary electrophoresis and lectin chromatography. The determined level of the glycosylation marker can be used to determined a clinical status. The clinical status can be, for example, cancer, precancerous condition, a benign condition or no condition. The clinical status can be also a particular stage of cancer such as tumor, lymph node or metastasis or a particular substage of tumor, lymph node or metastasis stage.

The identified glycosylation marker can be also used for an effect of therapy against cancer by comparing levels of the glycosylation marker before and after treatment of a subject with the therapy. One can also use the identified glycosylation marker for adjusting and/or optimizing a dose of a therapeutic agent or for testing a new therapy or a new therapeutic agent for treating cancer.

The identified glycosylation marker can be also used for isolating in a body fluid or a body tissue one or more glycoproteins that are specific biomarkers of cancer. The determined glycosylation markers can be also used for diagnosing, monitoring and/or prognosticating cancer using analytical techniques other than the techniques used to determine the glycosylation marker of cancer. Such other analytical techniques can be, for example, capillary electrophoresis or lectin chromatography.

The identified glycosylation marker(s) can be also used for identification and/or isolation of one or more glycoprotein biomarkers of cancer in a sample of a subject diagnosed with the cancer, i.e. for identification and/isolation of glycoprotein(s) that carry the glycosylation marker(s). In some embodiments, identification of such biomarkers utilizes 2 dimensional electrophoresis to separate proteins, including glycoproteins, in the biological sample into a plurality of spots. The spots of the plurality can be organized into individual spots or trains of spots. Each of the spots comprises one or more glycoforms of the proteins in the biological sample. Upon the separation, one can release glycans from one or more spots, i.e. unmodified glycans of the protein glycoforms of the one or more spots. Then, one can measure a glycosylation profile of the released glycoproteins searching for an altered level of the glycosylation marker(s). One then can select one or more glycoforms that correspond to the one or more spots, for which an altered level of the glycosylation marker(s) is found, as a biomarker of the physiological condition. The measuring of the glycosylation profile can be carried out by quantitative HPLC alone or in combination with mass spectrometry. In some embodiments, the one or more tested spots can correspond to glycoforms of highly abundant glycoprotein(s) such as IgG. Yet in some embodiments, the tested spots can correspond to glycoforms of glycoprotein(s) other than IgG. The glycoprofiles can be measured from the low abundant spot(s) such that each spot contains glycoprotein(s) in a quantity of less than about 100 ng, less than about 50 ng, less than about 10 ng, less than about 5 ng, less than about 2 ng or less than about 1 ng. The details of measuring glycosylation profiles from individual spots or trains of spots in 2D-gel are provided in PCT application No. PCT/IB2005/002531 to Dwek et. al. filed Jun. 24, 2005, and U.S. application "Automated Strategy for Identifying Physiological Glycosylation Marker(s)" to Dwek et. al. filed Apr. 26, 2006, which are both incorporated herein by reference in their entirety.

The identified biomarker(s) can be used for the same purposes as the glycosylation marker(s) such as diagnosing and monitoring cancer in a subject, monitoring an effect of a therapy on a subject by comparing a level of the marker before and after a treatment of the subject with a therapy.

Releasing Glycans

Glycans can be released from a sample of a subject such as a sample of a body fluid or a body tissue. The sample of the body fluid can be, for example, a sample of whole serum, blood plasma, urine, seminal fluid, seminal plasma, feces or saliva. The released glycans can be N-glycans or O-glycans.

In some embodiments, releasing a glycan pool of glycoproteins from a sample of a sample can be carried out without purifying the glycoproteins. In other words, the released glycans are glycans of all or substantially all of the glycoproteins present in the sample rather than of one or more purified and isolated glycoproteins.

In some embodiments, substantially all of the glycoproteins can mean all the glycoproteins that are recovered, yet in some embodiments substantially all of the glycoproteins can mean all the glycoproteins except those that are specifically removed. Releasing glycans can be carried out without exposing the sample to hydrazinolysis. In some embodiments, releasing glycans can be carried out from a very small sample of a body fluid. In some embodiments, samples of a body fluid can be less than 100 microliters, yet preferably less than 50 microliters, yet more preferably less than 20 microliters, yet more preferably less than 10 microliters, yet most preferably less than 5 microliters. The present methods of releasing can be optimized to work with body fluid samples of less than 1 microliters.

In some embodiments, releasing glycans can comprise releasing glycans from total glycoproteins the sample in solution. Yet in some embodiments, releasing glycans can comprise immobilizing total glycoproteins of the sample, for example, on protein binding membrane or in a gel. The protein binding membrane can be any protein binding membrane, for example, polyvinyldene fluoride (PVDF) membrane, nylon membrane or Polytetrafluoroethylene (PTFE) membrane. In some embodiments, releasing glycans can further comprise releasing glycans from the total glycoproteins immobilized on the protein binding membrane or in the gel. When released glycans are N-linked glycans, releasing glycans from the immobilized glycoproteins can be carried out using enzymatic release with, for example, peptide N glycosidase F. When the glycoproteins are immobilized in the gel, releasing glycans can comprise separating the gel into a plurality of bands and selecting one or more bands from the plurality of bands from which the glycans are subsequently released (in gel band method). In some embodiments, releasing glycans from the gel can be carried out from the total gel, i.e. without separating gel into the bands. In some embodiments, releasing glycans is carried out by chemical release methods, such as β-elimination or ammonia-based β-elimination, which can be used for releasing N-linked or O-linked glycans from glycoproteins in solution or from glycoproteins immobilized on protein binding membrane. For using the methods of this invention in a high throughput format, it may be preferred to release a glycan pool from total glycoproteins immobilized in a gel or on a protein binding membrane as it can allow to use smaller samples of body fluid or body tissue.

The details of some of the release methods and their applicability to both N-glycans and O-glycans are discussed below, however, it should be understood that the present invention is not limited to the discussed below release methods.

In-gel-band: This method can be used for N-glycan release from single glycopeptides in sodium dodecyl sulphate polyacrylamide gel electrophoresis (SDS PAGE) gel bands and is based on the method described in Kuster, B., Wheeler, S. F., Hunter, A. P., Dwek, R. A. and Harvey, D. J. (1997) "Sequencing of N-linked oligosaccharides directly from protein gels: in-gel deglycosylation followed by matrix-assisted laser desorption/ionization mass spectrometry and normal-phase high-performance liquid chromatography." *Anal-Biochem* 250: 82-101, incorporated herein by reference in its entirety. Samples can be reduced and alkylated by adding 4 μl of 5× sample buffer (5× sample buffer: 0.04 g Bromophenol blue, 0.625 ml 0.5M Tris (6 g for 100 ml) adjusted to pH 6.6 with HCl, 1 ml 10% SDS, 0.5 ml glycerol, in 2.875 ml water), 2 μl of 0.5M dithiothreitol (DTT) and water to make up to 20 μl in total, incubated at 70° C. for 10 min, then alkylated by addition of 2 μl of 100 mM iodoacetamide and incubated for 30 min in the dark at room temperature. Samples can be then separated on SDS-PAGE gels after which the proteins are stained with Coomassie brilliant blue, the band of interest is excised and destained. Subsequently, the gel band can be cut into 1 mm$^3$ pieces and frozen for 2 hours or more (this can help break down the gel matrix). This gel band can be then washed alternatively with 1 ml of acetonitrile then 1 ml of digestion buffer (20 mM NaHCO$_3$ pH 7), which can be repeated twice before the gel plug can be then dried. PNGase F buffer solution (30 μl of 100 U/ml) is added (this is enough for 10-15 mm$^3$ gel), more enzyme solution is added if larger gel bands can be used. The PNGaseF and gel pieces can be incubated overnight at 37° C. The supernatant can be recovered along with 3×200 μl water washes (with sonication with gel pieces for 30 mins each) followed by an acetonitrile wash (to squeeze out the gel), another water wash and a final acetonitrile wash. Samples can be filtered through a 0.45 μm LH Millipore filter and dried down for fluorescent labeling.

In-gel-block: To avoid the problems with clean up of samples following solution phase enzymatic glycan release an in-gel-block release from protein mixtures can be used. Briefly, the whole protein mixture (e.g. serum or plasma) can be reduced and alkylated as in the In-gel band oligosaccharide release described above, then set into 15% SDS-gel mixture but without bromophenol blue. A total volume of gel of 185 μL can be used (initially set into a 48 well plate, then removed for cutting up) with 300 μl of 100 U/ml of PNGaseF. The washing procedures can be similar to those used for in-gel-band release. Washing of gel can allow separation of the glycan pool from the parent proteins and thus provides glycans suitable for fluorescent labeling and further HPLC analysis. The in-gel-block procedure can be more suitable for automated glycan release than in-solution PNGaseF release, and can be the preferred method for high throughput glycan analysis.

This in-gel-block method has been further modified to work with smaller amounts of gel set into a 96 well plate. One can reduce and alkylate 5 μl of serum, in a polypropylene 96 well flat bottomed microplate, then set the sample into a gel-block by adding 30% (w/w) acrylamide: 0.8% (w/v) bis-acrylamide stock solution (37.5:1) (Protogel ultrapure protein and sequencing electrophoresis grade, gas stabilised; National Diagnostics, Hessle, Hull, UK), 1.5M Tris pH 8.8, 10% SDS, 10% APS (ammonium peroxodisulphate) and finally TEMED (N,N,N,N'-Tetramethyl-ethylenediamine) mixing then leave it to set. The gel blocks can be then transferred to a filter plate (Whatman protein precipitation plate) then washed with acetonitrile followed by 20 mM $NaHCO_3$. The gel pieces can be then dried in a vacuum centrifuge, incubated with 1% formic acid at for 40 min and then re-dried. The N-glycans can be released incubating with PNGaseF solution (Roche Diagnostics GmbH, Mannheim, Germany. The released glycans can be collected into a 2 ml square tapered polypropylene 96 well plate by washing the gel pieces with water followed by acetonitrile. The released glycans can be dried then labeled by incubating with 2-AB labelling solution (LudgerTag 2-AB labelling kit), for 2 hours at 65° C. Excess 2AB can be removed using a HILIC solid phase extraction (SPE) micro-elution plate (Waters) in a vacuum manifold. The labeled glycans can then eluted into a 2 ml 96 well then dried and redissolved them in 50 mM ammonium formate and acetonitrile ready for HPLC.

Enzymatic release of N-glycans from PVDF membranes. The glycoproteins in reduced and denatured serum samples can be attached to a hydrophobic PVDF membrane in a 96 well plate by simple filtration. The samples can be then washed to remove contaminates, incubated with PNGaseF to release the glycans based on the methods described in Papac, D. I., et. al. *Glycobiology* 8: 445-54, 1998, and in Callewaert, N., et. al. *Electrophoresis* 25: 3128-31, 2004, both incorporated herein by reference in their entirety. The N-glycans can be then washed from the bound protein, collected and dried down ready for fluorescent labeling. N-glycans can be released in situ from the glycoproteins by incubation with PNGaseF and by chemical means. The 2AB labeled N-glycans can be cleaned by SPE as in the in-gel-block method.

Chemical release of N- and O-glycans. In contrast to the advantages that enzymatic release of N-glycans can afford to N-glycan analysis, no enzymatic methodology currently exists for the release of structurally intact O-glycans. Chemical release by reductive β-elimination can require the concomitant reduction of the released oligosaccharides to their alditol derivatives (Amano, J. et. al. *Methods Enzymol* 179: 261-70, 1989) to prevent degradation (peeling). This reduction precludes the use of any post-release labeling so that detection is limited to mass spectrometry, pulsed amperometric detection and/or radioactivity.

Ammonia-based β-elimination can be used to release both N- and O-glycans by a modification of the classical β-elimination (Huang, Y. et. al. *Analytical Chemistry* 73: 6063-6069, 2001) which can be applied to glycoproteins in solution or on PVDF membranes. Ammonia-based β-elimination can be done from PVDF membranes. This strategy, can be optimized for high throughput, and can provide a powerful approach for releasing both N- and O-glycans in their correct molar proportions and in an open ring form suitable for post-release labeling.

Release of N- and O-glycans from protein binding PVDF membranes by ammonia based beta-elimination. Samples of glycoprotein, mixtures of glycoproteins, whole serum or other body fluids can be reduced and alkylated as in the in-gel-band method. Protein binding PVDF membranes (Durapore 13 mm×0.45 μm HVHP, Millipore) in Swinnex filter holders (Millipore) can be pre-washed with 2×2.5 ml water using an all-polypropylene 2.5 ml syringe (Sigma), followed by a syringe full of air to remove most of the liquid from the membrane. The reduced and alkylated sample can be then applied directly to the membrane and left to bind for 5 min before washing by pushing through 2×2.5 ml water slowly with a syringe, followed by a syringe full of air to remove most of the liquid from the membrane. The filter with the bound glycoprotein samples can be then carefully removed from the filter holder and placed in a 1.5 ml screw capped polypropylene tube with a molded PTFE cap. 1 ml of ammonium carbonate saturated 29.2% aqueous ammonium hydroxide, plus 100 mg ammonium carbonate can be added to the tube. This can be incubated for 40 hours at 60° C., then cooled in the fridge. The liquid can be then transferred to a clean tube and evaporated to dryness. The released glycans can be re-dissolved in water and re-dried until most of the salts are removed. 100 μl of 0.5M boric acid can be added to the glycans and incubated at 37° C. for 30 min. The glycans can be then dried under vacuum, 1 ml methanol added, re-dried, a further 1 ml methanol can be added and re-dried to remove the boric acid.

Quantitatively Analyzing the Glycans

Labeling of glycans. In some embodiments, upon releasing, the glycans can be labeled with, for example, a fluorescent label or a radioactive label. The fluorescent label can be, for example, 2-aminopyridine (2-AP), 2-aminobenzamide (2-AB), 2-aminoanthranilic acid (2-AA), 2-aminoacridone (AMAC) or 8-aminonaphthalene-1,3,6-trisulfonic acid (ANTS). Labeling of glycans with fluorescent labels is described, for example, by Bigge, J. C., et. al. "Nonselective and efficient fluorescent labeling of glycans using 2-amino benzamide and anthranilic acid." *Anal Biochem* 230: 229-38, 1995, incorporated herein reference in its entirety, and Anumula, K. R. (2000). High-sensitivity and high-resolution methods for glycoprotein analysis. Analytical Biochemistry 283: 17-26, incorporated by reference in its entirety. Fluorescent labels can label all glycans efficiently and non-selectively and can enable detection and quantification of glycans in the sub picomole range. The choice of fluorescent label depends on the separation technique used. For example, a charged label is specifically required for capillary electrophoresis. In particular, 2-AB label can be preferred for chromatographic, enzymatic and mass spectroscopic processes and analyses, while 2-AA label can be preferred for electrophoretic analyses. Unlabelled glycans can be also detected by, for example, mass spectrometry, however, fluorescent labelling may aid glycan ionisation, see e.g. Harvey, D. J. (1999). "Matrix-assisted laser desorption/ionization mass spectrometry of carbohydrates." *Mass Spectrom Rev* 18: 349-450.; Harvey, D. J. (2000). Electrospray mass spectrometry and fragmentation of N-linked carbohydrates derivatized at the reducing terminus. J Am Soc Mass Spectrom 11: 900-915.

Measuring glycoprofile of the released glycans. Glycoprofile of the glycans means a presentation of particular glycan structures in the glycans. Measuring glycoprofile of the glycans can be carried out by quantitative analytical technique, such as chromatography, mass spectrometry, electrophoresis or a combination thereof. In particular, the chromatographic technique can be high performance anion exchange chromatography (HPAEC), weak ion exchange chromatography (WAX), gel permeation chromatography (GPC), high performance liquid chromatography (HPLC), normal phase high performance liquid chromatography (NP-HPLC), reverse phase HPLC (RP-HPLC), or porous graphite carbon HPLC (PGC-HPLC). The mass spectrometry technique can be, for example, matrix assisted laser desorption/ionization time of flight mass spectrometry (MALDI-TOF-MS), electrospray ionization time of flight mass spectrometry (ESI-TOF-MS), positive or negative ion mass spectrometry or liquid chromatography mass spectrometry (LC-MS). The electrophoretic technique can be, for example, gel electrophoresis or capillary electrophoresis. The use of these quantitative analytical techniques for analyzing glycans is described, for example, in the following publications:

1) Guile, G. R., Wong, S. Y. and Dwek, R. A. (1994). "Analytical and preparative separation of anionic oligosaccharides by weak anion-exchange high-performance liquid chromatography on an inert polymer column." *Analytical Biochemistry* 222: 231-5 for HPLC, incorporated herein by reference in its entirety;
2) Butler, M., Quelhas, D., Critchley, A. J., Carchon, H., Hebestreit, H. F., Hibbert, R. G., Vilarinho, L., Teles, E., Matthijs, G., Schollen, E., Argibay, P., Harvey, D. J., Dwek, R. A., Jaeken, J. and Rudd, P. M. (2003). "Detailed glycan analysis of serum glycoproteins of patients with congenital disorders of glycosylation indicates the specific defective glycan processing step and provides an insight into pathogenesis." *Glycobiology* 13: 601-22, for MALDI-MS, NP-HPLC and ESI-liquid chromatography/MS, incorporated herein by reference in its entirety;
3) Jackson, P., Pluskal, M. G. and Skea, W. (1994). "The use of polyacrylamide gel electrophoresis for the analysis of acidic glycans labeled with the fluorophore 2-aminoacridone." *Electrophoresis* 15: 896-902, for polyacrylamide gel electrophoresis (PAGE), incorporated herein by reference in its entirety;
4) Hardy, M. R. and Townsend, R. R. (1994). "High-pH anion-exchange chromatography of glycoprotein-derived carbohydrates." *Methods Enzymol* 230: 208-25., for HPAEC using pulsed amperometric detection (PAD), incorporated herein by reference in its entirety;
5) Callewaert, N., Contreras, R., Mitnik-Gankin, L., Carey, L., Matsudaira, P. and Ehrlich, D. (2004). "Total serum protein N-glycome profiling on a capillary electrophoresis-microfluidics platform." *Electrophoresis* 25: 3128-31 for capillary electrophoresis, incorporated herein by reference in its entirety;
6) Guile, G. R., Rudd, P. M., Wing, D. R., Prime, S. B. and Dwek, R. A. (1996). "A rapid high-resolution high-performance liquid chromatographic method for separating glycan mixtures and analyzing oligosaccharide profiles." *Anal Biochem* 240: 210-26, for HPLC, incorporated herein by reference in its entirety;
7) Caesar, J. P., Jr., Sheeley, D. M. and Reinhold, V. N. (1990). "Femtomole oligosaccharide detection using a reducing-end derivative and chemical ionization mass spectrometry." *Anal Biochem* 191: 247-52, for LC-MS, incorporated herein by reference in its entirety;
8) Mattu, T. S., Royle, L., Langridge, J., Wormald, M. R., Van den Steen, P. E., Van Damme, J., Opdenakker, G., Harvey, D. J., Dwek, R. A. and Rudd, P. M. (2000). "O-glycan analysis of natural human neutrophil gelatinase B using a combination of normal phase-HPLC and online tandem mass spectrometry: implications for the domain organization of the enzyme." *Biochemistry* 39: 15695-704, for NP-HPLC and MS, incorporated herein by reference in its entirety;
9) Royle, L., Mattu, T. S., Hart, E., Langridge, J. I., Merry, A. H., Murphy, N., Harvey, D. J., Dwek, R. A. and Rudd, P. M. (2002). "An analytical and structural database provides a strategy for sequencing O-glycans from microgram quantities of glycoproteins." *Anal Biochem* 304: 70-90, for NP-HPLC and MS, incorporated herein by reference in its entirety;
10) Anumula, K. R. and Du, P. (1999). "Characterization of carbohydrates using highly fluorescent 2-aminobenzoic acid tag following gel electrophoresis of glycoproteins." *Anal Biochem* 275: 236-42, for gel electrophoresis, incorporated herein by reference in its entirety;
11) Huang, Y. and Mechref, Y. (2001). "Microscale nonreductive release of O-linked glycans for subsequent analysis through MALDI mass spectrometry and capillary electrophoresis." *Analytical Chemistry* 73: 6063-6069, for a combination of MALDI-MS and capillary electrophoresis, incorporated herein by reference in its entirety;
12) Burlingame, A. L. (1996). "Characterization of protein glycosylation by mass spectrometry." *Curr Opin Biotechnol* 7: 4-10, for mass spectrometry, incorporated herein by reference in its entirety;
13) Costello, C. E. (1999). "Bioanalytic applications of mass spectrometry." *Curr Opin Biotechnol* 10: 22-8, for mass spectrometry, incorporated herein by reference in its entirety;
14) Davies, M. J. and Hounsell, E. F. (1996). "Comparison of separation modes of high-performance liquid chromatography for the analysis of glycoprotein- and proteoglycan-derived oligosaccharides." *J Chromatogr A* 720: 227-33, for HPLC, incorporated herein by reference in its entirety;
15) El Rassi, Z. (1999). "Recent developments in capillary electrophoresis and capillary electrochromatography of carbohydrate species." *Electrophoresis* 20: 3134-44, for capillary electrophoresis and capillary electrochromatography, incorporated herein by reference in its entirety;
16) Kuster, B., Wheeler, S. F., Hunter, A. P., Dwek, R. A. and Harvey, D. J. (1997). "Sequencing of N-linked oligosaccharides directly from protein gels: in-gel deglycosylation followed by matrix-assisted laser desorption/ionization mass spectrometry and normal-phase high-performance liquid chromatography." *Anal-Biochem* 250: 82-101, for NP-HPLC and MALDI-MS, incorporated herein by reference in its entirety;
17) Reinhold, V. N., Reinhold, B. B. and Chan, S. (1996). "Carbohydrate sequence analysis by electrospray ionization-mass spectrometry." *Methods Enzymol* 271: 377-402, for ESI-MS, incorporated herein by reference in its entirety;
18) Mattu, T. S., Pleass, R. J., Willis, A. C., Kilian, M., Wormald, M. R., Lellouch, A. C., Rudd, P. M., Woof, J. M. and Dwek, R. A. (1998). "The glycosylation and structure of human serum IgA1, Fab, and Fc regions and the role of N-glycosylation on Fc alpha receptor interactions." *Journal of Biological Chemistry* 273: 2260-72, for WAX and NP-HPLC, incorporated herein by reference in its entirety.
19) Callewaert, N., Schollen, E., Vanhecke, A., Jaeken, J., Matthijs, G., and Contreras, R. (2003). Increased fucosylation and reduced branching of serum glycoprotein N-glycans in all known subtypes of congenital disorder of glycosylation I. Glycobiology 13: 367-375, incorporated herein by reference in its entirety;
20) Block, T. M. Comunale, M. A., Lowman, M., Steel, L. F., Romano, P. R., Fimmel, C., Tennant, B. C. London, A. A. Evans, B. S. Blumberg, R. A. Dwek, T. S. Mattu and A. S. Mehta, "Use of targeted glycoproteomics to identify serum glycoproteins that correlate with liver cancer in woodchucks and humans". PNAS USA (2005) 102, 779-784, incorporated herein by reference in its entirety;
21) D. J. Harvey, Fragmentation of negative ions from carbohydrates: Part 1; Use of nitrate and other anionic adducts for the production of negative ion electrospray spectra from N-linked carbohydrates, *J. Am. Soc. Mass Spectrom.*, 2005, 16, 622-630, incorporated herein by reference in its entirety;

22) D. J. Harvey, Fragmentation of negative ions from carbohydrates: Part 2, Fragmentation of high-mannose N-linked glycans, *J. Am. Soc. Mass Spectrom.*, 2005, 16, 631-646, incorporated herein by reference in its entirety;

23) D. J. Harvey, Fragmentation of negative ions from carbohydrates: Part 3, Fragmentation of hybrid and complex N-linked glycans, *J. Am. Soc. Mass Spectrom.*, 2005, 16, 647-659, incorporated, herein by reference in its entirety.

Although many techniques can be used for measuring glycoprofiles, in the method of determining one or more glycosylation markers of a physiological condition such as a disease or a stage of disease, it can be preferred to measure glycoprofiles by high performance liquid chromatography (HPLC) alone or in combination with mass spectrometry. For example, measuring glycoprofiles can be performed by gel electrophoresis (see Jackson, P., Pluskal, M. G. and Skea, W. (1994). "The use of polyacrylamide gel electrophoresis for the analysis of acidic glycans labeled with the fluorophore 2-aminoacridone." *Electrophoresis* 15: 896-902); HPAEC using pulsed amperometric detection (PAD) (Townsend, R. R., Hardy, M. R., Hindsgaul, O. and Lee, Y. C. (1988). "High-performance anion-exchange chromatography of oligosaccharides using pellicular resins and pulsed amperometric detection." *Anal Biochem* 174: 459-70; and Hardy, M. R. and Townsend, R. R. (1994). "High-pH anion-exchange chromatography of glycoprotein-derived carbohydrates." *Methods Enzymol* 230: 208-25); or capillary electrophoresis (see El Rassi, Z. (1999). "Recent developments in capillary electrophoresis and capillary electrochromatography of carbohydrate species." *Electrophoresis* 20: 3134-44), however, these techniques are not ideally suited to large-scale automation, nor do they provide full quantitative structural analysis. In general they have poor detection limits, low reproducibility and are restricted by the inherent difficulty of obtaining full structural characterization of the oligosaccharides and the lack of predictability that is required to enable the preliminary assignments to be made to novel structures.

Measuring a glycoprofile by quantitative HPLC, i.e. measuring a glycoprofile of fluorescently labeled glycans such as 2AB labeled glycans by HPLC can allow accurate quantification and structural assignment of the glycan structures in the glycan pool by integration of the peaks in the chromatogram. The fluorescent labeling is non-selective and adds one fluorescent label per glycan, thus, allowing a direct correlation between fluorescence measured as peak area or height and the amount of each glycan. For an HPLC measured glycoprofile, glycan structures present in the analyzed glycan pool are separated based on their elution time. For NP-HPLC, the elution times can be converted to glucose units by comparison with a standard dextran hydrolysate ladder. An HPLC measured glycoprofile can trace all glycan structures present in a glycan pool in correct molar proportions. Polar functional groups of stationary phase of HPLC can interact with the hydroxyl groups of the glycans in a manner that is reproducible for a particular monosaccharide linked in a specific manner. For example, the contribution of the outer arm fucose addition is much greater than the addition of a core fucose residue; a core fucose residue always contributes 0.5 glucose units (gu) to the overall elution position. The characteristic incremental values associated with different monosaccharide additions can allow the preliminary assignment of a predicted structure for a particular peak present in the glycoprofile. This structure can be then confirmed by digestion with exoglycosidase arrays and/or mass spectrometry. Other techniques, such as capillary electrophoresis are not as predictable as NP-HPLC. Although, CE migration times can be calibrated with standards, the migration times of unknown structures can not be easily predicted.

Measuring glycoprofiles by NP-HPLC can be also preferred for the following reason. Digestion of a glycan pool with one or more exoglycosidases removes monosaccharide residues and, thus, decreases the retention times or associated gu values in the glycoprofile measured by NP-HPLC. In some embodiments, this can enable the segregation of the peaks that are associated with one or glycosylation markers by shifting away peaks that are not related to the glycosylation changes away from the measured region of the glycoprofile.

In some embodiments, measuring glycoprofiles can be carried out using reverse phase high performance liquid chromatography. For RP-HPLC measured glycoprofiles, the elution times can be converted into arabinose units using a standard arabinose ladder. The use of RP-HPLC for measuring glycosylation profiles is described, for example, in Guile, G. R., Harvey, D. J., O'Donnell, N., Powell, A. K., Hunter, A. P., Zamze, S., Fernandes, D. L., Dwek, R. A., and Wing, D. R. (1998). "Identification of highly fucosylated N-linked oligosaccharides from the human parotid gland. European Journal of Biochemistry" 258: 623-656; Royle, L., Mattu, T. S., Hart, E., Langridge, J. I., Merry, A. H., Murphy, N., Harvey, D. J., Dwek, R. A., and Rudd, P. M. (2002). An analytical and structural database provides a strategy for sequencing O-glycans from microgram quantities of glycoproteins. Analytical Biochemistry 304: 70-90., incorporated herein by reference. RP-HPLC measured glycoprofiles can be used to complement glycoprofiles measured by NP-HPLC. For example, RP-HPLC can separate bisected glycan structures from glycan structures that do not contain bisecting N-acetylglucoamine residue. In NP-HPLC measured glycoprofiles these structures can be too close to be resolved. In some embodiments, measuring glycoprofiles by RP-HPLC can comprise using one or more buffers. The mobile phase can be used, for example, to improve the reproducibility of the measurement. The buffer can be, for example, solvent A: 50 mM of ammonium formate adjusted to pH5 with triethylamine and solvent B: solvent A and acetonitrile mixed 50/50. In some embodiments, HPLC can be used as a preparative method for collecting glycans, i.e. HPLC can be used to isolate unusual glycans for further analysis, by e.g. mass spectrometry, as well as for obtaining parameters for a glycan database.

In some embodiments, each of the glycoprofiles can be presented as a plurality of peaks corresponding to glycan structures in the glycans. In the method of determining one or more glycosylation markers, a peak ratio means a ratio between any one or more peaks and any other one or more peaks within the same glycosylation profile. In the method of determining a glycosylation marker, comparing peak ratios can mean comparing peaks intensities or comparing integrated areas under the peaks. In some embodiments of the method of determining glycosylation marker, comparing peak ratios can be carried for glycans of the tested and control samples which were not digested with one or more exoglycosidases. In some embodiments, comparing peak ratios can be carried out on the glycans which were digested with one or more exoglycosidases. In some embodiments, comparing peak ratios can be carried out for the glycans which were not digested with exoglycosidase and for the glycans digested with one or more exoglycosidases.

In some embodiments, measuring glycoprofiles with HPLC can be complemented with a mass spectrometry measurement. Complementary mass spectrometry data, such as MALDI, ESI or LC/MS) can serve, for example, for validation HPLC measured glycoprofiles as a separate orthogonal technique able to resolve the structures of more complex glycans when a sufficient amount of sample of a body fluid or a body tissue is available. Mass spectrometry used in combination with HPLC can be a powerful tool for structural analysis of glycoproteins. Mass spectrometry alone can be used for structural analysis of glycans providing monosaccharide composition of glycans. However, mass spectrometry used by itself does not distinguish isobaric monosaccharide (and hence oligosaccharides or glycans) and does not provide the information on monosaccharide linkage in glycans. The LC-MS/(MS) techniques can provide the most informative data out of the mass spectrometry technique, see Caesar, J. P., Jr., Sheeley, D. M. and Reinhold, V. N. (1990). "Femtomole oligosaccharide detection using a reducing-end derivative and chemical ionization mass spectrometry." *Anal Biochem* 191: 247-52; Mattu, T. S., Pleass, R. J., Willis, A. C., Kilian, M., Wormald, M. R., Lellouch, A. C., Rudd, P. M., Woof, J. M. and Dwek, R. A. (1998). "The glycosylation and structure of human serum IgA1, Fab, and Fc regions and the role of N-glycosylation on Fc alpha receptor interactions." *Journal of Biological Chemistry* 273: 2260-72; and Royle, L., Mattu, T. S., Hart, E., Langridge, J. I., Merry, A. H., Murphy, N., Harvey, D. J., Dwek, R. A. and Rudd, P. M. (2002). "An analytical and structural database provides a strategy for sequencing O-glycans from microgram quantities of glycoproteins." *Anal Biochem* 304: 70-90. In some embodiments, measuring glycoprofiles by LC/MS can comprise using the LC stage of LC/MS not only for cleanup and preliminary separation of glycans before they enter the MS stage of LC/MS but for obtaining preliminary assignment of glycan structures in the glycans. This can be accomplished, for example, by using NP-HPLC matrix, for example NP-HPLC with TSK gel amide 80 matrix, in the LC column of LC/MS. In NP-HPLC with TSK gel amide 80 matrix, hydroxyl groups of glycans interact with the amide functionality, therefore, the elution order is determined by the number of hydroxyl groups in a particular glycan, its molecular confirmation and its relative solubility in the mobile phase.

In some embodiments, when the glycan pool comprises charged glycans, the glycan pool can be fractioned into several aliquots based upon charge. Fractioning of the glycan pool can be carried out, for example, by weak ion exchange (WAX) chromatography. Each WAX aliquot can be then analyzed independently by NP-HPLC combined with exoglycosidase digestions. Measuring glycoprofiles by WAX HPLC is described, for example, in Guile, G. R., Wong, S. Y. and Dwek, R. A. (1994). "Analytical and preparative separation of anionic oligosaccharides by weak anion-exchange high-performance liquid chromatography on an inert polymer column." *Analytical Biochemistry* 222: 231-5.

Measuring glycoprofile of the glycans with the above described methods can allow detecting a particular glycan structure present in the glycans in subpicomole levels. Accordingly, in some of the embodiments, measuring glycoprofiles of the glycans is carried out using a technique able to detect a glycan structure present in the glycans in amount of 1 picomole, preferably 0.1 picomole, yet more preferably 0.01 picomole. Measuring glycoprofile of the glycans can comprise constructing a database of glycan structures of the glycans. The parameters of this database can be, for example, glycan structure along with: elution times (from HPLC data); mass and composition (from MS data); experimentally determined and/or predicted glycan structures, elution times, mass and composition, following treatment with exoglycosidase enzymes; experimentally determined and/or predicted glycan structures, mass and composition following MS fragmentation. The database can, for example, make preliminary and final assignments of the glycan structures as well as recommend the appropriate exoglycosidase arrays to confirm preliminary assignments. The use of databases in measuring glycoprofiles is described, for example, in the following references:

1) Mattu, T. S., Royle, L., Langridge, J., Wormald, M. R., Van den Steen, P. E., Van Damme, J., Opdenakker, G., Harvey, D. H., Dwek, R. A. and Rudd, P. M. (2000). "The O-glycan analysis of natural human neutrophil gelatinase B using a novel strategy combining normal phase-HPLC and on-line tandem mass spectrometry: implications for the domain organization of the enzyme." *Biochemistry* 39: 15695-704.", incorporated herein by reference in its entirety;

2) Royle, L., Mattu, T. S., Hart, E., Langridge, J. I., Merry, A. H., Murphy, N., Harvey, D. J., Dwek, R. A. and Rudd, P. M. (2002). "An analytical and structural database provides a strategy for sequencing O-glycans from microgram quantities of glycoproteins." *Anal Biochem* 304: 70-90, incorporated herein by reference in its entirety;

3) Butler, M., Quelhas, D., Critchley, A. J., Carchon, H., Hebestreit, H. F., Hibbert, R. G., Vilarinho, L., Teles, E., Matthijs, G., Schollen, E., Argibay, P., Harvey, D. J., Dwek, R. A., Jaeken, J. and Rudd, P. M. (2003). "Detailed glycan analysis of serum glycoproteins of patients with congenital disorders of glycosylation indicates the specific defective glycan processing step and provides an insight into pathogenesis." *Glycobiology* 13: 601-22, incorporated herein by reference in its entirety;

4) Peracaula, R., Royle, L., Tabares, G., Mallorqui-Fernandez, G., Barrabes, S., Harvey, D. J., Dwek, R. A., Rudd, P. M. and de Llorens, R. (2003). "Glycosylation of human pancreatic ribonuclease: differences between normal and tumor states." *Glycobiology* 13: 227-44, incorporated herein by reference in its entirety;

5) Peracaula, R., Tabares, G., Royle, L., Harvey, D. J., Dwek, R. A., Rudd, P. M. and de Llorens, R. (2003). "Altered glycosylation pattern allows the distinction between prostate-specific antigen (PSA) from normal and tumor origins." Glycobiology 13: 457-70.

Exoglycosidase Digestion to Amplify/Segregate Glycosylation Markers

In some embodiments, the released glycans can be subjected to further enzymatic digestion with one or more enzymes. The enzymatic digestion can be done using any suitable enzymes, such as glycosidases. Examples of suitable glycosidases include, but are not limited to, sialidase, β-galactosidase, fucosidase α1-6,2>>3,4, α1-3,4, α1-2 fucosidase, alpha-amylase, beta-amylase, glucan 1,4-alpha-glucosidase, cellulase, endo-1,3(4)-beta-glucanase, inulinase, endo-1,4-beta-xylanase, oligosaccharide alpha-1,6-glucosidase, dextranase, chitinase, polygalacturonase, lysozyme, exo-alpha-sialidase, alpha-glucosidase, beta-glucosidase, alpha-galactosidase, beta-galactosidase, alpha-mannosidase, beta-mannosidase, beta-fructofuranosidase, alpha,alpha-trehalase, beta-glucuronidase, xylan endo-1,3-beta-xylosidase, amylo-alpha-1,6-glucosidase, hyaluronoglucosaminidase, hyaluronoglucuronidase, xylan 1,4-beta-xylosidase, beta-D-fucosidase, glucan endo-1,3-beta-D-glucosidase, alpha-L-rhamnosidase, pullulanase, GDP-glucosidase, beta-L-rhamnosidase, fucoidanase, glucosylceramidase, galactosylceramidase, galactosylgalactosylglucosylceramidase, sucrose alpha-glucosidase, alpha-N-acetylgalactosaminidase, alpha-N-acetylglucosaminidase, alpha-L-fucosidase, beta-N-acetylhexosaminidase, beta-N-acetylgalactosaminidase, cyclomaltodextrinase, alpha-L-arabinofuranosidase, glucuronosyl-disulfoglucosamine glucuronidase, isopullulanase, glucan 1,3-beta-glucosidase, glucan endo-1,3-alpha-glucosidase, glucan 1,4-alpha-maltotetrahydrolase, mycodextranase, glycosylceramidase, 1,2-alpha-L-fucosidase, 2,6-beta-fructan 6-levanbiohydrolase, levanase, quercitrinase, galacturan 1,4-alpha-galacturonidase, isoamylase, glucan 1,6-alpha-glucosidase, glucan endo-1,2-beta-glucosidase, xylan 1,3-beta-xylosidase, licheninase, glucan 1,4-beta-glucosidase, glucan endo-1,6-beta-glucosidase, L-iduronidase, mannan 1,2-(1,3)-alpha-mannosidase, mannan endo-1,4-beta-mannosidase, fructan beta-fructosidase, agarase, exo-poly-alpha-galacturonosidase, kappa-carrageenase, glucan 1,3-alpha-glucosidase, 6-phospho-beta-galactosidase, 6-phospho-beta-glucosidase, capsular-polysaccharide endo-1,3-alpha-galactosidase, beta-L-arabinosidase, arabinogalactan endo-1,4-beta-galactosidase, cellulose 1,4-beta-cellobiosidase, peptidoglycan beta-N-acetylmuramidase, alpha,alpha-phosphotrehalase, glucan 1,6-alpha-isomaltosidase, dextran 1,6-alpha-isomaltotriosidase, mannosyl-glycoprotein endo-beta-N-acetylglucosaminidase, glycopeptide alpha-N-acetylgalactosaminidase, glucan 1,4-alpha-maltohexaosidase, arabinan endo-1,5-alpha-L-arabinosidase, mannan 1,4-beta-mannobiosidase, mannan endo-1,6-beta-mannosidase, blood-group-substance endo-1,4-beta-galactosidase, keratan-sulfate endo-1,4-beta-galactosidase, steryl-beta-glucosidase, strictosidine beta-glucosidase, mannosyl-oligosaccharide glucosidase, protein-glucosylgalactosylhydroxylysine glucosidase, lactase, endogalactosaminidase, mucinaminylserine mucinaminidase, 1,3-alpha-L-fucosidase, 2-deoxyglucosidase, mannosyl-oligosaccharide 1,2-alpha-mannosidase, mannosyl-oligosaccharide 1,3-1,6-alpha-mannosidase, branched-dextran exo-1,2-alpha-glucosidase, glucan 1,4-alpha-maltotriohydrolase, amygdalin beta-glucosidase, prunasin beta-glucosidase, vicianin beta-glucosidase, oligoxyloglucan beta-glycosidase, polymannuronate hydrolase, maltose-6'-phosphate glucosidase, endoglycosylceramidase, 3-deoxy-2-octulosonidase, raucaffricine beta-glucosidase, coniferin beta-glucosidase, 1,6-alpha-L-fucosidase, glycyrrhizinate beta-glucuronidase, endo-alpha-sialidase, glycoprotein endo-alpha-1,2-mannosidase, xylan alpha-1,2-glucuronosidase, chitosanase, glucan 1,4-alpha-maltohydrolase, difructose-anhydride synthase, neopullulanase, glucuronoarabinoxylan endo-1,4-beta-xylanase, mannan exo-1,2-1,6-alpha-mannosidase, anhydrosialidase, alpha-glucosiduronase, lacto-N-biosidase, 4-alpha-D-{(1->4)-alpha-D-glucano}trehalose trehalohydrolase, limit dextrinase, poly(ADP-ribose) glycohydrolase, 3-deoxyoctulosonase, galactan 1,3-beta-galactosidase, beta-galactofuranosidase, thioglucosidase, ribosylhomocysteinase, beta-primeverosidase. Most preferably, enzymatic digestion is carried out with one or more exoglycosidases listed in table 1.

TABLE 1

| Exoglycosidase Specificities - | |
|---|---|
| Sialidase α-(2-3,6,8) | Cleaves all non-reducing terminal branched and unbranched sialic acids |
| Sialidase α-(2-3) | Cleaves the non-reducing terminal alpha-(2-3) unbranched sialic acid residues from complex carbohydrates and glycoproteins. |
| α-(1-3,4,6)-galactosidase | Cleaves α-(1-3)-, α-(1-4)-and α-(1-6)-linked, non-reducing terminal galactose from complex carbohydrates and glycoproteins. Fucose linked to the penultimate N-acetylglucosamine will block cleavage of the galactose. |
| β-(1-4)-galactosidase | Cleaves Non-reducing terminal β-(1-4)-galactose. Fucose linked to the penultimate N-acetylglucosamine will block cleavage of the galactose. |

TABLE 1-continued

| Exoglycosidase Specificities - | |
|---|---|
| β-(1-3,4,6)-galactosidase | Cleaves all β1-3 and β1-4 linked non-reducing, terminal galactose. Fucose linked to the penultimate N-acetylglucosamine will block cleavage of the galactose. |
| β-(1-3,6)-galactosidase | Cleaves β-(1-3)- and β-(1-6)-linked, non-reducing terminal galactose from complex carbohydrates and glycoproteins. Fucose, but not sialic acid, linked to the penultimate N-acetylglucosamine will block cleavage. |
| β-N-acetylglucosaminidase | Cleaves all non-reducing terminal β-linked N-acetylglucosamine. Bisecting GlcNAc slows the reaction |
| β-N-acetylhexosaminidase | Cleaves all non-reducing terminal β-linked N-acetylglucosamine and N-acetylgalacosamine. Bisecting GlcNAc slows the reaction |
| α-(1-2,3,6)-mannosidase | Cleaves all α-(1-2,3,6)-linked mannose. |
| α-(1-6)-core mannosidase | Cleaves unbranched, terminal non-reducing mannose linked alpha-(1-6) to the mannosyl chitobiose core. The presence of a branched mannose alpha-(1-3) will inhibit the removal of the 1-6 mannose. |
| α-(1-3,4)-fucosidase | Cleaves non-reducing terminal branched fucose when linked alpha-(1-3) or alpha-(1-4) to GlcNAc. |
| α-(1-6>2>>3,4)-fucosidase | Cleaves non-reducing terminal branched fucose when linked alpha-(1-6) to GlcNAc or Gal. Will also cleave alpha-(1-2) and alpha-(1-3,4) with reduced efficiency |
| α-(1-2)-fucosidase | Cleaves non-reducing terminal branched fucose when linked alpha-(1-2) to a Gal. |

In some embodiments, the enzymatic digestion can be sequential, so not all monosaccharides are removed at once. The digested glycans can be analyzed after each digestion step to obtain a glycosylation profile. In some embodiments, the enzymatic digestion can be digestion with an array comprising one or more exoglycosidases. Digestion with an array means using a panel of exoglycosidases together in a single digestion on a pool of glycans. Each exoglycosidase enzyme removes specific terminal monosaccharides attached in defined linkages. Digestion of a glycan pool with one or more exoglycosidases which can be used in any combination is important for two reasons. First, digestion with one or more exoglycosidase can segregate the glycosylation marker by shifting glycans that do not contain the marker from the measured region of the glycoprofile. Second, digestion with one or more exoglycosidase can be used to amplify the markers by digesting away monosaccharides that are attached to some of the markers oligosaccharides but are not essential feature of the markers. For example, a glycosylation marker of which the essential part consists of a LeX epitope may be present on more than one glycan structure, e.g., it can be present on both oligosaccharide A that has a core fucose and on oligosaccharide B that does not have a core fucose. By digesting away the core fucose, structures A and B merge, thus, amplifying the signal associated with the glycosylation marker.

Using the Glycosylation Markers of Cancer to Identify and Isolate Glycoproteins

In some embodiments, the determined glycosylation marker of cancer can be used for identifying and isolating one or more glycoprotein biomarkers, i.e. glycoproteins that are specific for particular type of cancer. The glycoprotein biomarker of the disease carries the glycosylation marker of cancer. The isolation of the glycoprotein biomarkers of the cancer can be carried out using lectins or monoclonal antibodies.

For example, lectins were used to isolate gp73, a glycoprotein marker of hepatitis B associated with liver cancer in "Use of targeted glycoproteomics to identify serum glycoproteins that correlate with liver cancer in woodchucks and humans". T. M. Block, M. A. Comunale, M. Lowman, L. F. Steel, P. R. Romano, C. Fimmel, B. C. Tennant, W. T. London, A. A. Evans, B. S. Blumberg, R. A. Dwek, T. S. Mattu and A. S. Mehta (2005) Proc. Natl. Acad. Sci. USA, 102, 779-784.

The methodology for diagnosing and monitoring cancer can be illustrated in more details by the following examples, however, it should be understood that the present invention is not limited thereto.

Example 1

Breast Cancer

Breast cancer is the leading cause of cancer deaths in females with a million new cases diagnosed annually, worldwide, see e.g. Mazor, Y., Keydar, I., and Benhar, I. Mol Immunol. 2005 January; 42(1):55-69, incorporated herein by reference in its entirety. Humanization and epitope mapping of the H23 anti-MUC1 monoclonal antibody reveals a dual epitope specificity. The panel of serum markers which is currently in practice mainly comprises of CA15-3 and/or CA27.29 in combination with CEA (Carcinoembryogenic Antigen), see e.g. Duffy, M. J. (1999) CA15.3 and related mucins as circulating markers in breast cancer. Ann. Clin. Biochem., 36, 579-586; Perkins, G. L., Slater, E. D., Sanders, G. K., and Prichard, J. G. (2003) Serum tumor markers. American Family Physician, 68, 1075-1082, both incorporated herein by reference. Both CA15-3 and CA27.29 are directed against MUC1, see Klee, G. G. and Schreiber, W. E. (2004) MUC1 gene-derived glycoprotein assays for monitoring breast cancer (CA 15-3), CA 27.29, BR): Are They Measuring the Same Antigen? Arch. Pathol. Lab. Med., 128, 1131-1135, a mucin which is overly expressed and aberrantly glycosylated in breast cancer, see Taylor-Papadimitriou, J., Burchell, J., Miles, D. W., and Dalziel, M. (1999) MUC1 and cancer. Biochem. Biophys. Acta., 1455, 301-313.

Analysis of Glycosylation Profiles of Glycans Released from whole sera of a breast cancer patient and healthy controls. Glycosylation profiles of glycans released from whole serum of controls and breast cancer patients were compared to detect a potential glycosylation marker differentiating the two groups. In addition to that, total serum glycans from a single breast cancer patient, but at two different stages of malignancy, were analyzed to correlate the detected marker with breast cancer progression.

Samples of serum from breast cancer patient were obtained from a single donor (LD) with her consent before and after mastectomy. The healthy control serum was obtained from pooled blood bank serum.

Glycoproteins in reduced and denatured serum samples were set into gel-blocks, washed and incubated overnight with PNGaseF. The released N-glycans were then washed from the bound protein, collected and dried down ready for fluorescent labeling. Released glycans were labeled with 2-aminobenzamide (2-AB) fluorescent label with or without a commercial kit (e.g. Ludger Ltd, Oxford, UK) as described in Bigge, J. C., Patel, T. P., Bruce, J. A., Goulding, P. N., Charles, S. M., and Parekh, R. B. (1995). Nonselective and efficient fluorescent labeling of glycans using 2-amino benzamide and anthranilic acid. Analytical Biochemistry 230: 229-238, incorporated herein by reference in its entirety, and run by normal phase high performance liquid chromatography (NP-HPLC) on a 4.6×250 mm TSK Amide-80 column (Anachem, Luton, UK) using a Waters 2695 separations module equipped with a Waters 2475 fluorescence detector (Waters, Milford, Mass., USA) as described in Guile, G. R., Rudd, P. M., Wing, D. R., Prime, S. B., and Dwek, R. A. (1996). A rapid high-resolution high-performance liquid chromatographic method for separating glycan mixtures and analyzing oligosaccharide profiles. Analytical Biochemistry 240: 210-226, incorporated herein by reference in its entirety. Prior to further NP-HPLC analysis, glycans were digested with a series of exoglycosidases.

FIG. 1A shows glycosylation profiles of undigested glycans released from serum of a healthy control and a breast cancer patient. Sample 1 of the breast cancer patient is taken before surgery and Sample 2 is taken after surgery with liver metastases. Both glycosylation profiles from breast cancer samples demonstrate an increase in the amount of the peak at 10.5 glucose units (GU) compared to the glycosylation profile from the control sample (FIG. 1A). The 10.5 GU peak shifts down to 7.5 GU following digestion with sialidase, β1-3,4,6 galactosidase and α1-2 link specific fucosidase, and has a higher percentage in the patient sample compared to the control (FIG. 1B). The peak at GU 7.5 is then completely digested by the combination of sialidase, β1-4 galactosidase (in place of β1-3,4,6 galactosidase) and α1-3/4 link specific fucosidase in the control and patient samples indicating the presence of outer arm α1-3/4 fucosylation. This demonstrates an increased amount of Lewis X epitope in the cancer (FIG. 1C). After surgery the marker decreased from 3.9% to 3.3% suggesting that the prognosis may be poor.

Conclusion: a glycosylation marker of breast cancer was identified by comparing glycosylation profiles of glycans released from whole serum of breast cancer patient and of glycans released from whole serum of a healthy control. Digestion with exoglycosidases amplifies/segregates the glycosylation marker of breast cancer. The glycosylation marker is elevated in disease.

A Longitudinal study of the identified glycosylation marker in one patient. The identified glycosylation marker A3G1F is the outer arm α1-3 linked fucosylated tri-antennary N-linked glycan which is derived from Lewis x or Sialyl Lewis X by treating the N-glycans released from total serum glycoproteins with a combination of sialidase and β-galactosidase which segregates this structure from others. This glycosylation marker is not the native sugar—it is the digestion product—and exoglycosidase digestions enable the amplification and segregation the marker for quantitative HPLC analysis.

Figure 2:
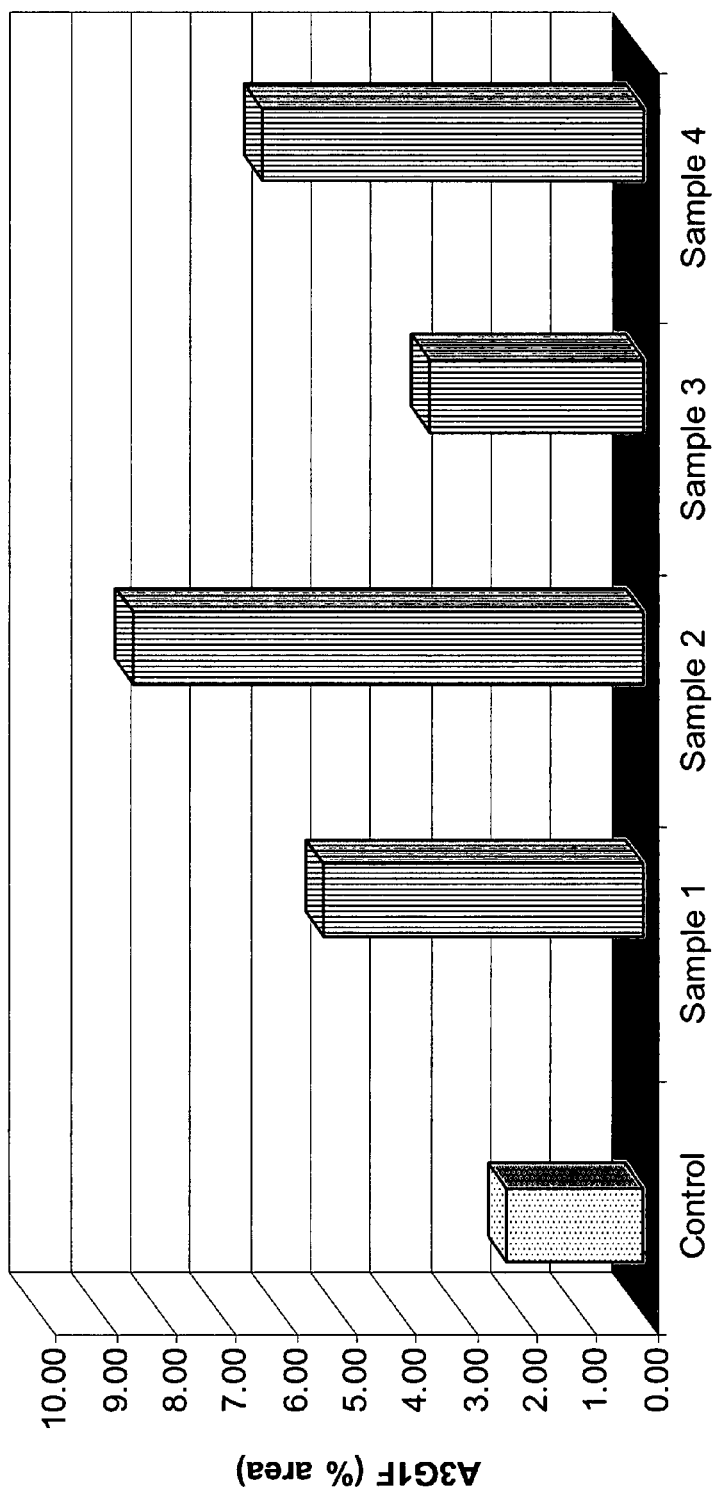
FIG. 2 demonstrates a longitudinal study of A3G1F marker in a single breast cancer patient compared to control.

FIG. 2 presents a longitudinal study of the levels of the glycosylation marker (A3G1F) in the same breast cancer patient as in FIG. 1 at four different stages of breast cancer. The % areas of sLex on the tri-antennary structure in the N-glycan pool released from whole serum was measured after a sialidase, B-galactosidase and α1,2 fucosidase (Abs+Btg+Xmf). All four patient samples have at least a 2-fold increase in the % and the fluctuation shown. Thus, A3G1F glycosylation marker can be used for prognostic applications in breast cancer patients.

Figure 3:
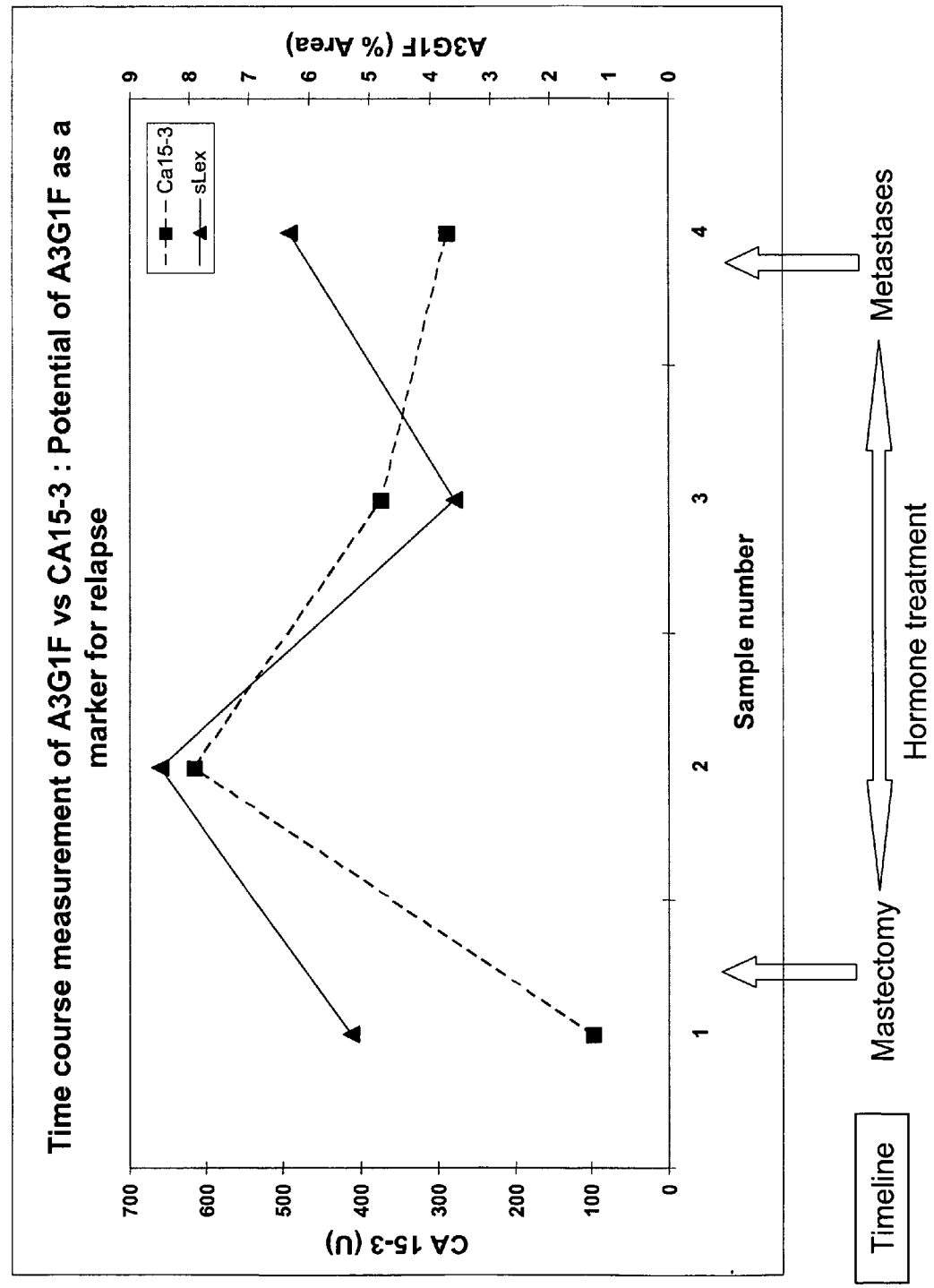
FIG. 3 shows a time course measurement of A3G1F marker vs. CA15-3 marker.

FIG. 3 defines the four stages and compares the levels of glycosylation marker A3G1F with those of carbohydrate antigen 15-3 (CA 15-3) protein biomarker. The disease stage at which each sample was collected is shown in a timeline: stage 1: mastectomy, stage 2: mastectomy under hormonal treatment, stage 3: mastectomy under hormonal treatment; stage 4: metastasis detected. At stage 4, when metastasis was detected, the level of A3G1F increases whereas the level of CA15-3 marker was still decreasing. Thus, quantification of the A3G1F glycosylation biomarker may provide an earlier indicator of metastasis.

Identification of Protein Biomarkers. The established A3G1F marker can be used to identify a protein biomarker of breast cancer. The A3G1F is derived mainly from SLex attached to a tri-sialylated tri-antennary N-glycan therefore, one can use an anti-SLex antibody to identify the glycoprotein(s) in Breast Cancer serum which carry such a structure.

Figure 4:
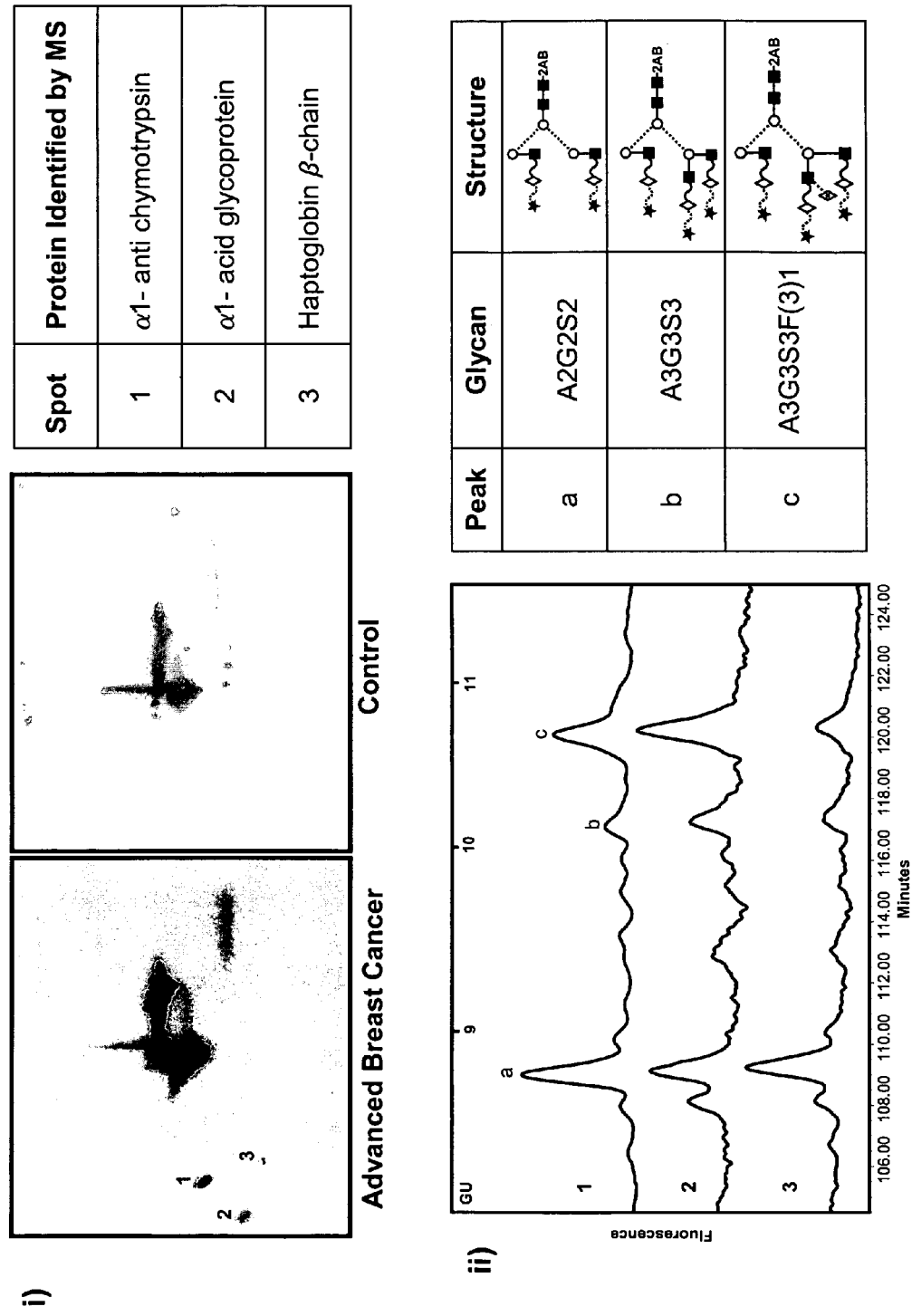
FIG. 4 illustrates identification on 2D-PAGE of glycoproteins carrying the glycan biomarker in breast cancer serum.

Whole serum (80 μg) of control and breast cancer patient were subjected to 2D gel electrophoresis according to the procedure described in details the example 3 of the application "AUTOMATED STRATEGY FOR IDENTIFYING PHYSIOLOGICAL MARKER(S)" to Dwek et. al. filed Apr. 26, 2006, and incorporated herein by reference in its entirety. The gels on control and breast cancer patients were mini-gels (1st dimension—7 cm IPG strip pI 3-10, 2nd dimension—8.5×6.5 cm 4-12%) prepared in duplicates. The proteins from one gel of each sample were transferred to a PVDF membrane and blotted using the anti-sialyl Lewis X antibody (KM93, CalBiochem). These western blots with KM93 highlighted the glycoproteins carrying the SLex epitope. FIG. 4(i) shows selected highlighted spots on the blot for control and breast cancer samples. The breast cancer sample presented in FIG. 4(i) is the sample from the same patient at stage 4 as in FIGS. 2&3. Three highlighted protein spots on the gel for breast cancer sample in FIG. 4(i) have been identified by mass spectrometry as 1-α1 anti chymotrypsin, 2-α1 acid glycoprotein, 3-haptoglobin B chain and/or Complement C3.

N-glycans were released from each of the three spots by PNGaseF digestion and subjected to detailed glycosylation analysis by HPLC. The glycosylation profiles from each of the three glycoproteins were found to have the sialyl Lewis x structure, see FIG. 4(ii).

Thus, measuring glycoprofile from 2D-gel spot(s) can enable the identification of aberrantly glycosylated protein glycoforms in breast cancer serum as biomarkers for prognosis and diagnosis of patients.

Example 2

Pancreatic Cancer

Pancreatic cancer is the fifth leading cause of cancer death in the United States killing about 30,000 people each year. About an equal number of new cases of pancreatic cancer are diagnosed each year, which corresponds to about 9 new cases per 100,000 people. While treatment options have advanced, pancreatic cancer remains very difficult to treat as evidenced by the high mortality rate. Specifically, the 1-year survival rate of pancreatic cancer patients is 19% and the 5-year survival rate is 4%. This high mortality rate is due, in part, to the fact that about 80% of pancreatic cancers are already metastatic at the time of diagnosis. See Yeo et al., CURRENT PROBLEMS IN CANCER 26(4): (2002), 176-275.

A variety of serum tumor markers, especially CA119-9, a Lewis blood group-related mucin, have been proposed for diagnosing and monitoring of this type of neoplasia, but their application remains experimental, see Lillemoe, K. D., Yeo, C. J., and Cameron, J. L. (2000) Pancreatic cancer: state-of-the art care. Cancer J. Clin., 50, 241-268, incorporated herein by reference in its entirety.

In pancreatic cancer, both cell surface glycoproteins and secreted pancreatic ribonuclease (RNase 1) are aberrantly glycosylated, see e.g. Peracaula R, Royle L, Tabarés G, Mallorquí-Fernández G, Barrabés S, Harvey D, Dwek R A, Rudd, P M, de Llorens R. (2003) "Glycosylation of human pancreatic ribonuclease: differences between normal and tumour states", Glycobiology, 13, 227-244, incorporated herein by reference in its entirety. In particular, one of the most distinctive features was that RNase 1 glycans from established adenocarcinoma pancreatic cell lines, Capan-1 and MDA-Panc-3, contained sialylated structures, which were completely absent in the RNase 1 from healthy pancreas. These differences provide distinct epitopes that were clearly detected using monoclonal antibodies against carbohydrate antigens. Monoclonal antibodies to Lewis$^y$ reacted only with normal pancreatic RNase 1, whereas, in contrast, monoclonal antibodies to sialyl-Lewis$^x$ and sialyl-Lewis$^a$ reacted only with RNase 1 secreted from the tumor cells.

Analysis of Glycans Released from whole sera of Pancreatic cancer patients and corresponding healthy controls. In this study, glycosylation profiles of glycans released from whole serum of controls and pancreatic cancer patients were compared to detect a potential glycosylation marker differentiating the two groups.

A sample of serum from pancreatic cancer patient was obtained from a patient with neoplastic cancer, high creatinine levels and vascular affectations. A sample of healthy control serum was obtained as discarded clinical material from individuals undergoing routine employee health screening.

Preparation of glycans for analysis and experimental details of the analysis are the same as in the Example 1.

Resulting glycosylation profiles are presented on FIG. 5. In particular, FIG. 5(A) demonstrates glycosylation profiles of glycans digested with sialidase, β-galactosidase and fucosidase with the arm specificity α1-6,2>>3,4. The glycosylation profile from the pancreatic cancer sample has additional peaks not present in the control sample. The glycans were further subjected to a digestion with α1-3,4 fucosidase. The results of this digestion are presented on FIG. 5(B). The digestion with α1-3,4 fucosidase removes the additional peaks previously present in the pancreatic cancer sample but not in the control sample, thus, demonstrating that there is an increase in the outer arm α1-3,4 fucosylation for the glycans released from the whole serum of the pancreatic cancer patient.

Conclusion: a glycosylation marker of pancreatic cancer was identified by comparing glycosylation profiles of glycans released from whole serum of pancreatic cancer patients and of glycans released from whole serum of a healthy control. The glycosylation marker of pancreatic cancer can be amplified/segregated by digesting with an array of exoglycosidases.

The data presented on FIGS. 5(C)-(D) are for two patients with localized pancreatic cancer. Preparation of glycans for analysis and experimental details of the analysis are the same as in the Example 1.

FIG. 5(C) shows NP-HPLC glycosylation profiles of glycans released from a pooled control and two pancreatic patients' sera. The glycoprofiles from the patients' samples show the increase in the amount of the outer arm fucosylated trisialylated triantennary glycan.

FIG. 5(D) demonstrates amplification, segregation and identification of the marker A3G1F by NP-HPLC after digestion of the entire glycan pool with (i) sialidase, β galactosidase and fucosidase with the arm specificity α1-6, 2>>3,4 and (ii) following further digestion with α1-3,4 fucosidase. The data in FIG. 5(D) show that, after digestion, A3G1F glycosylation marker is present in higher amounts in the patients' samples. The structure of A3G1F was confirmed by digestion with α1-3,4 fucosidase.

Example 3

Prostate Cancer

Prostate cancer is the most common cancer in men in Western countries and is the second leading cause of cancer death. In fact, prostate cancer is the sixth most common cause of death overall for men in the U.S. It is estimated that 232,090 new cases of prostate cancer will be diagnosed in 2005 with 30,350 deaths attributed to prostate cancer. One in six men will be diagnosed with prostate cancer, and 1 in 33 men will die of the disease.

As other types of cancer, prostate cancer is classified based on how far the cancer has progressed. A number of scales exist, but the TNM (tumor, lymph node, and metastases) scale is a standard scale commonly referred to in the medical literature. In the T1 stage, the tumor cannot be seen on scans or felt during examination. These tumors are typically detected using a needle biopsy after an abnormal PSA test, which is discussed in more detail below. At the T2 stage, the tumor can be seen or felt but remains inside the prostate gland. T3 stage tumors have broken through the capsule of the prostate gland, and T4 stage tumors have spread into other body organs, such as the rectum or bladder. The N stages follow similar classifications of tumor spread as follows: (a) N0—no cancer cells found in any lymph nodes; (b) N1—one positive lymph node smaller than 2 cm across; (c) N2—more than one positive lymph node or a tumor that is between 2 and 5 cm across; and (d) N3—any positive lymph node that is bigger than 5 cm across. Finally, a cancer is M0 if no cancer has spread outside the pelvis and M1 if cancer has spread outside the pelvis.

Prostate-specific antigen (PSA), a glycoprotein secreted by prostate cells that is found in serum in prostate pathologies, is the currently used tumour marker for prostate cancer diagnostics, see e.g. Diamandis E. (1998) Prostate-Specific antigen: Its Uselfulness in Clinical Medicine. TEM, 9, 310-316, incorporated herein by reference. However, PSA is still not specific enough for diagnosing prostate cancer, as other prostatic pathologies, like benign prostate hyperplasia (BPH), can show serum PSA elevations. Different approaches have been tried to improve this situation but so far only with limited success, see e.g. Brawer M K. (1999) Prostate-specific antigen: current status. CA Cancer J Clin, 49, 264-281, incorporated herein by reference in its entirety.

Glycosylation has been found to be different between purified PSA from seminal plasma and when secreted by the tumour prostate cell line LNCaP, see e.g. Peracaula R, Tabarés G, Royle L, Harvey D J, Dwek R A, Rudd, P M, de Llorens R. (2003) Altered glycosylation pattern allows the distinction between Prostate Specific Antigen (PSA) from normal and tumor origins, Glycobiology, 13, 457-470.

Analysis of Glycans Released from Whole sera of Prostate cancer patients and corresponding healthy controls. In this study, glycosylation profiles of glycans released from whole serum of healthy control and prostate cancer patient were compared to detect a potential glycosylation marker differentiating the two groups. Samples of tumor serum were obtained from a patient with prostate cancer with elevated levels of serum PSA (1.8 micrograms/ml). The healthy control serum was obtained from pooled blood bank serum.

Preparation of glycans for analysis and experimental details of the analysis are the same as in the Example 1.

Resulting glycosylation profiles are presented on FIG. 6. In particular, FIG. 6(A) demonstrates the glycosylation profiles of undigested glycans, FIG. 6 (B) demonstrates the glycosylation profiles of glycans digested with array of sialidase, β-galactosidase, and fucosidase with the arm specificity α1-6,2>>3,4, while FIG. 6(C) demonstrates the glycosylation profiles of glycans further digested with α1-3,4 fucosidase. For undigested glycans, a difference between glycosylation profiles from prostate cancer samples and from healthy control sample was observed in the region of ~9.5 to ~11 GU (FIG. 6(A)). Following the digestion with sialidase, β-galactosidase, and fucosidase α1-6,2>>3,4, the glycosylation profile from prostate cancer sample demonstrates a stronger peak (in intensity and peak area) at ~6.5 GU compared to the control glycosylation profile. The stronger peak at ~6.5 GU indicates a higher content of tetra antennary glycans in the prostate cancer sample. Further digestion with α1-3,4 fucosidase removes/reduces the peaks at 7-7.5 GU in the glycosylation profiles of prostate cancer samples, while the peaks of the control sample are almost not affected. This indicates that there is an increase in the outer arm α1-3,4 fucosylation in the glycans released from a whole serum of prostate cancer patient.

Conclusion: a glycosylation marker of prostate cancer was identified by comparing glycosylation profiles of glycans released from whole serum of prostate cancer patient and of glycans released from whole serum of a healthy control. Digestion of glycans with exoglycosidases amplifies/segregates the glycosylation marker of prostate cancer.

Figure 6E:
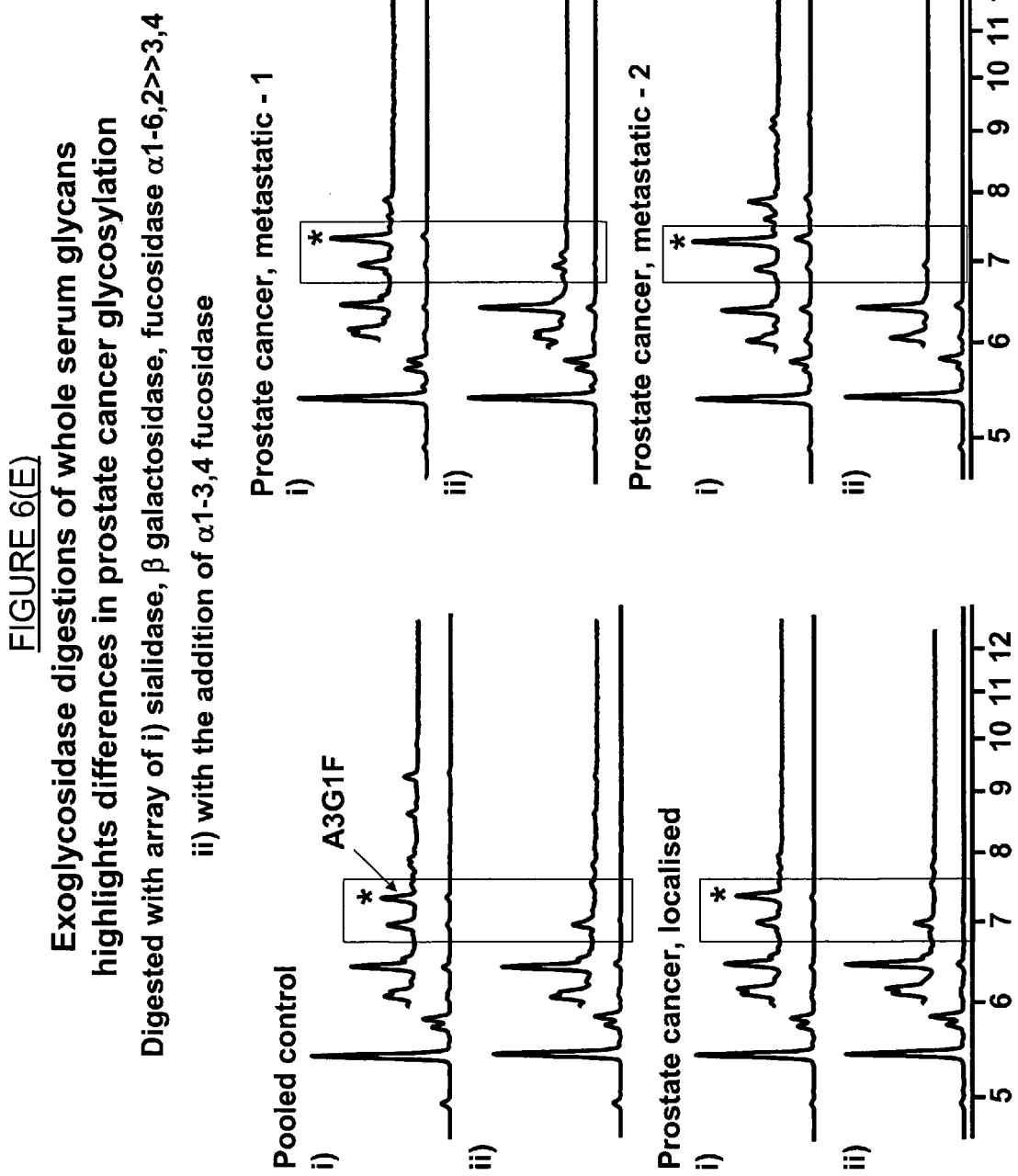
FIG. 6 (A)-(E) illustrate determination of a glycosylation marker for prostate cancer.

The data presented in FIGS. 6(D)-(E) correspond to one patient having a localized prostate cancer and two patients having prostate cancer in metastasis stage. Preparation of glycans for analysis and experimental details of the analysis are the same as in the Example 1.

FIG. 6(D) presents NP HPLC glycosylation profiles of glycans released from a pooled control and two prostate patients' sera. The glycoprofiles of the patients' samples show the increase in the amount of the outer arm fucosylated trisialylated triantennary glycan.

FIG. 6(E) demonstrates amplification, segregation and identification of the glycosylation marker tri-antennary glycan with one outer arm fucose and galactose (A3G1F) by NP HPLC after digestion of the entire glycan pool with i) sialidase, b galactosidase and fucosidase with the outer arm α1-6, 2>>3,4 and ii) further digestion with α1-3,4 fucosidase. The data on FIG. 6(E) show that, after digestion, the glycosylation marker A3G1F is present in higher amounts in the patient samples. The structure of A3G1F was confirmed by digestion with α1-3,4 fucosidase.

Example 4

Hepatocellular Carcinoma in Hepatitis C virus Infected Patients

Hepatitis C is a serious worldwide health problem. Globally, an estimated 170 million people have been infected with the hepatitis C virus (HCV). Chronic HCV infection can result in fibrosis, cirrhosis, hepatocellular carcinoma (HCC) and hepatic decompensation. HCV related end-stage liver disease is the leading indication for liver transplants in the United States. There is no vaccine available against HCV. Liver biopsy is considered the gold standard for assessment of liver damage and determining the need of treatment, although it is expensive, invasive, and subject to interpretive variation. Treatment for HCV, a 6 to 12 month course of pegylated interferon and ribavirin, can lead to potentially severe side effects and only eradicates HCV in about half of patients. Current surveillance techniques are suboptimal for early diagnosis of HCC, which occurs in 1-4% of cirrhosis annually. There is an urgent need for non-invasive testing methods, as well as the identification of prognostic markers and more effective screening methods for early diagnosis of HCC. Glycosylation profiles of glycans released from whole serum of controls and hepatitis C virus (HCV) infected patients with hepatocellular carcinoma were compared to detect a potential glycosylation marker differentiating the two groups. Two samples from healthy controls, including both pooled and individual sera, were analyzed. A specific database containing NP-HPLC serum glycan profiles for both sialylated and neutral glycans contains more than 38 glycans. The same procedure was applied to patient sera and the glycosylation marker of hepatocellular carcinoma in HCV patients was identified by comparison the database of glycans released from whole serum of HCV infected patients with the database of glycans released from whole serum of healthy controls Samples of serum from HCV infected patients with hepatocellular carcinoma were obtained from HCV infected patients with moderate or severe fibrosis/cirrhosis. Samples of healthy control serum were obtained as discarded clinical material from individuals undergoing routine health screening Preparation of glycans for analysis and experimental details of the analysis are the same as in the Example 1.

FIG. 7 presents NP-HPLC profiles of glycans released from control sample Con_9 and from sample of HCV infected patient with hepatocellular carcinoma HCV_42. On FIG. 7, panel (A) corresponds to glycoprofiles of whole serum glycans not exposed to any exoglycosidase digestion, panel (B) to glycoprofiles following digestion with an array of α2-3,6,8-sialidase, β1-4 galactosidase and β-N-acetylglucosaminidase. Panel (C) of FIG. 7 demonstrates that the marker correlated with the diagnosis of hepatocellular carcinoma in HCV patients is the percentage of core fucosylated glycans measured after digestion with α2-3,6,8-sialidase, α1-4 galactosidase and β-N-acetylglucosaminidase. Healthy control sera contains between 15 and 17% of these glycans, while sera of HCV infected patients with hepatocellular carcinoma contained more than 19% of these glycans. The correlation was also observed between the stage of the disease and the percentage of core fucosylated glycans measured after digestion with α2-3,6,8-sialidase, 1'-4 galactosidase and β-N-acetylglucosaminidase. HCV infected patients in moderate stage of hepatocellular carcinoma had the percentage of core fucosylated glycans measured after digestion with α2-3, 6,8-sialidase, β1-4 galactosidase and β-N-acetylglucosaminidase of 20-22%, while patients in severe stages of disease, such as severe fibrosis/cirrhosis, had this glycan marker above 25% on average.

Conclusion: a glycosylation marker of hepatocellular carcinoma in HCV patients was identified by comparing glycosylation profiles of glycans released from whole serum of HCV patients with hepatocellular carcinoma and of glycans released from whole serum of healthy controls. The glycosylation marker of hepatocellular carcinoma in HCV patients is the percentage of core fucosylated glycans measured after digestion with α2-3,6,8-sialidase, β1-4 galactosidase and β-N-acetylglucosaminidase. The marker correlates with the disease diagnosis and the disease severity. Digestion of glycans with exoglycosidases amplifies/segregates the glycosylation marker of hepatocellular carcinoma in HCV patients.

Example 5

Ovarian Cancer

Ovarian cancer is the fourth leading cause of cancer related deaths in women in USA and the leading cause of gynecologic cancer death. Ovarian cancer is characterized by few early symptoms, presentation at an advanced stage, and poor survival. Despite being one tenth as common as breast cancer, ovarian cancer is three times more lethal. It is estimated that in 2005 22,220 women will be newly diagnosed with ovarian cancer, and 16,210 will die from the disease, see Jemal, A., Murray, T., Ward, E., Samuels, A., Tiwari, R., Ghafoor, A., Feuer E. L. & Thun, M. J. (2005) *CA Cancer J. Clin.* 55, 10-30, incorporated hereby by reference in its entirety. The high mortality rate is due to the difficulties with the early detection of ovarian cancer. Indeed, ~80% of patients are diagnosed currently with advanced staged disease.

As other types of cancer, ovarian cancer is classified based on how far the cancer has progressed. A number of scales exist, but the TNM (tumor, lymph node, and metastases) scale is a standard scale commonly referred to in the medical literature. At T1 stage, cancer is confined to the ovaries—one or both. At T2 stage, cancer is in one or both ovaries and is extending into pelvic tissues and/or has also spread to the surface of the pelvic lining. At T3 stage, cancer is in one or both ovaries and has spread to the abdominal lining outside the pelvis. N categories indicate whether or not the cancer has spread to regional (nearby) lymph nodes and, if so, how many lymph nodes are involved. For ovarian cancer, N0 stage means no lymph node involvement and N1 stage means that cancer cells found in regional lymph nodes close to tumor. M categories indicate whether or not the cancer has spread to distant organs, such as the liver, lungs, or non-regional lymph nodes. For ovarian cancer, M0 stage means no distant spread is observed and M1 means that distant spread is present. Ovarian cancer is also often stages of disease from stage I (the least advanced) to stage IV (the most advanced stage). More details of grading ovarian and other cancers can be found, for example, at the American Cancer Society website.

Serum biomarkers that are elevated in women with ovarian cancer include carcinoembrionic antigen, ovarian cystadenocarcinoma antigen, lipid-associated sialic acid, NB/70, TAG 72.3, CA-15.3 and CA-125, see e.g. G. Mor et al., PNAS, v. 102, pp. 7677-7682, 2005. CA 125 is elevated in 82% of women with advanced ovarian cancer, however, it has a low predictive value for early stages of cancer, see Kozak et. al. PNAS, v. 100, pp. 12343-12348, 2003.

Analysis of Glycans Released from Whole sera of Ovarian cancer patients and corresponding healthy controls. In this study, glycosylation profiles of glycans released from whole serum of healthy control and ovarian cancer patient were compared to detect a potential glycosylation marker differentiating the two groups. Samples of tumor serum were obtained from a patient with advanced malignant tumor. The healthy control serum was obtained from pooled blood bank serum. Preparation of glycans for analysis and experimental details of the analysis are the same as in the Example 1.

Resulting glycosylation profiles are presented on FIG. 8(A)-(C). In particular, FIG. 8(A) demonstrates the glycosylation profiles of undigested glycans, FIG. 8(B) demonstrates the glycosylation profiles of glycans digested with sialidase, β1-3,4,6 galactosidase and α1-2 link specific fucosidase, while FIG. 8(C) demonstrates the glycosylation profiles of glycans further digested with sialidase, β1-4 galactosidase (in place of β1-3,4,6 galactosidase) and α1-3/4 link specific fucosidase. For undigested glycans, a difference between glycosylation profiles from ovarian cancer sample and from healthy control sample was observed in the region of ~9.5 to ~11 GU (FIG. 8(A)). In particular, a strong peak was observed ~10.5 GU in the ovarian cancer patient which was weaker in the control sample. Upon digestion with sialidase, β1-3,4,6 galactosidase and α1-2 link specific fucosidase, the ~10.5 GU peak shifted to ~7.5 GU (FIG. 8(B)). The 7.5 GU peak has a higher percentage (~11.8%) in the ovarian cancer sample than in the control sample. The peak at GU 7.5 is then completely digested by the combination of sialidase, β1-4 galactosidase (in place of β1-3,4,6 galactosidase) and α1-3/4 link specific fucosidase in the patient samples indicating the presence of outer arm α1-3 fucose (i.e. Lewis x epitope) (FIG. 8(C)).

Conclusion: a glycosylation marker of ovarian cancer was identified by comparing glycosylation profiles of glycans released from whole serum of ovarian cancer patient and of glycans released from whole serum of a healthy control. Digestion with exoglycosidases amplifies/segregates the glycosylation marker of ovarian cancer.

Glycosylation Analysis from Whole Serum 2D Gel Spots

Figure 10:
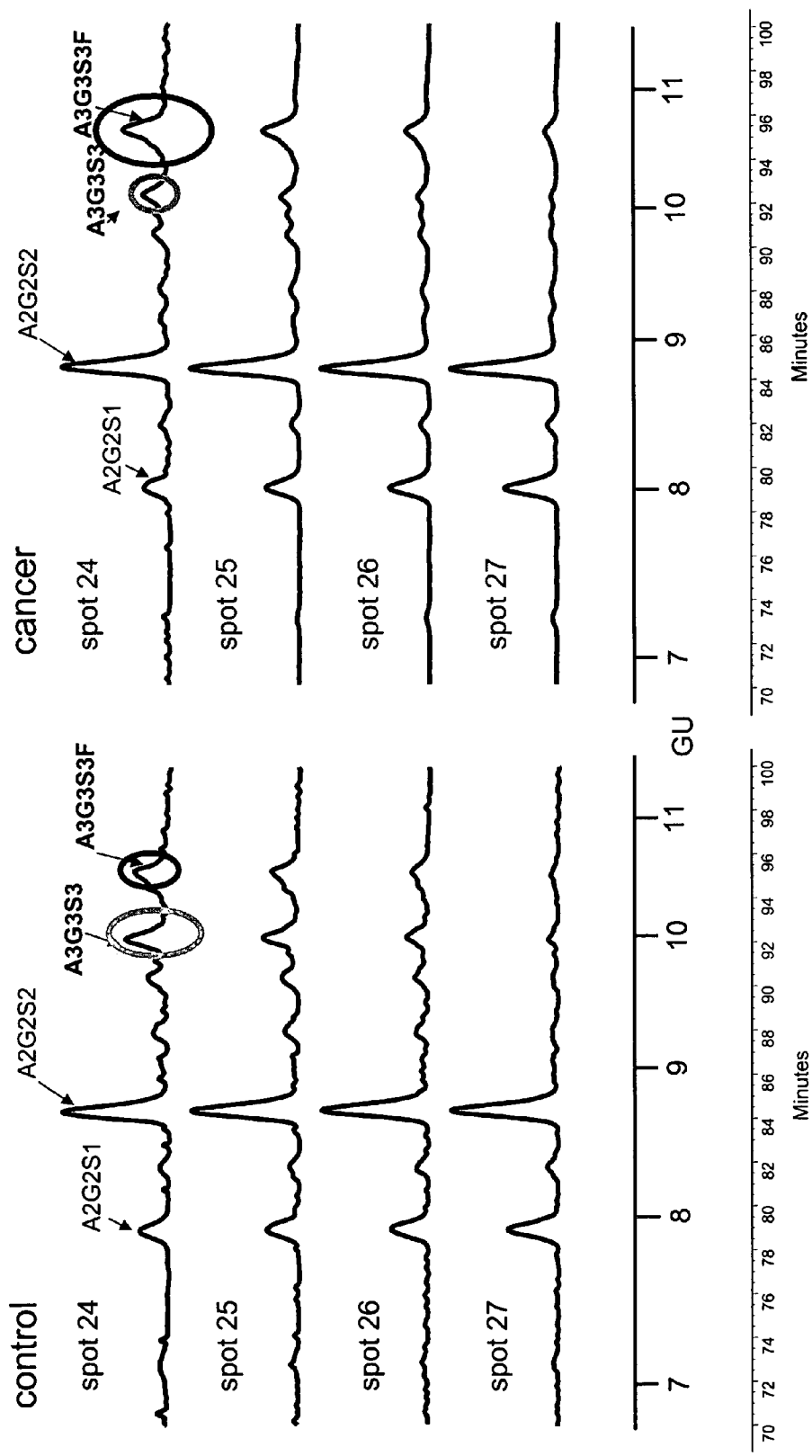
FIG. 10 illustrates glycosylation analysis of the train of spots from haptoglobin β-chain (FIG. 9) showing that different sub-populations of glycoprotein (glycoforms) are present in each spot of the train. The anlysis was carried out directly from the gel spots.

Whole serum (80 µg) of control and ovarian cancer patient were subjected to 2D gel electrophoresis according to the procedure described in details the example 3 of the application "AUTOMATED STRATEGY FOR IDENTIFYING PHYSIOLOGICAL MARKER(S)" to Dwek et. al. filed on the same day with the present application and incorporated herein by reference in its entirety. FIG. 9 shows 2D gel electrophoresis of serum highlighting the train of haptoglobin β-chain spots which were excised for glycosylation analysis. Since less than 2 µg of haptoglobin in total were loaded in the gels, each spot in the train contains less than 400 ng of protein. FIG. 10 shows NP-HPLC glycosylation profiles obtained from spots 24-27 of haptoglobin β chain train for control and ovarian cancer samples. The ratio of A3G3S3F to A3G3S3 is higher in the ovarian cancer haptoglobin β-chain spots, particularly for spot 24, compared to respective control spots.

Example 6

Cancer Glycosylation Marker Determined by Weak Ion Exchange Chromatography

2AB labelled glycans from a pooled control, prostate cancer, pancreatic cancer, ovarian cancer, uveal melanoma and breast cancer samples were also separated by weak anion exchange (WAX) HPLC into fractions dependent on the number of sialic acids present on the glycans (as described in Guile, G. R., Wong, S. Y. and Dwek, R. A. (1994). "Analytical and preparative separation of anionic oligosaccharides by weak anion-exchange high-performance liquid chromatography on an inert polymer column." *Analytical Biochemistry* 222: 231-5). These fractions were then run on NP HPLC. FIG. 11 shows the NP HPLC glycosylation profiles of the tri-sialylated fraction of glycans. The data in FIG. 11 demonstrate that the ratio of outer-arm-fucoslylated trisialylated triantennary glycan (A3G3S3F) to trisialylated triantennary glycan (A3G3S3) is higher in all the cancer samples compared to the pooled control, thus indicating the trend in a range of cancers for the fucosylated tri-antennary trisialylated glycan to be increased.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

Additional Embodiments

1. A method of determining one or more glycosylation markers of cancer comprising obtaining a diseased sample and a control sample, wherein the diseased sample is a sample from a subject diagnosed with cancer and the control sample is a sample from healthy control;

releasing a diseased glycan pool of total glycoproteins from the diseased sample and a control glycan pool of total glycoproteins from the control sample without purifying the glycoproteins and without exposing the diseased sample and the control sample to hydrazinolysis;

measuring a diseased glycoprofile of the diseased glycan pool and a control glycoprofile of the control glycan pool using chromatography, mass spectrometry or a combination thereof;

comparing the diseased glycoprofile and the control glycoprofiles to determine said one or more glycosylation markers of cancer.

2. The method of embodiment 1, wherein comparing the diseased glycoprofile and the control glycoprofile comprises comparing peak ratios in the diseased glycoprofile and in the control glycoprofile.

3. The method of embodiment 1, further comprising selecting a best glycosylation marker out of said one or more glycosylation markers of cancer, wherein the best glycosylation marker has a highest correlation with one or more parameters of the subject diagnosed with cancer.

4. The method of embodiment 3, wherein the parameters of the subject diagnosed with cancer are diagnosis, disease stage, disease severity, age, sex, medical history, response to therapy or a combination thereof.

5. The method of embodiment 3, wherein the parameter is diagnosis.

6. The method of embodiment 1, wherein the cancer is pancreatic cancer, prostate cancer, breast cancer, hepatocellular carcinoma, ovarian cancer, bladder cancer, renal cancer, colon cancer, stomach cancer or lung cancer.

7. The method of embodiment 1, wherein said cancer is pancreatic cancer.

8. The method of embodiment 1, wherein said cancer is prostate cancer.

9. The method of embodiment 1, wherein said cancer is breast cancer.

10. The method of embodiment 1, wherein said cancer is hepatocellular carcinoma.

11. The method of embodiment 1, wherein said cancer is ovarian cancer.

12. The method of embodiment 1, further comprising amplifying and segregating the glycosylation marker by digesting the diseased glycan pool and the control glycan pool with one or more exoglycosidases.

13. The method of embodiment 1, further comprising amplifying and segregating the glycosylation marker by sequential digesting the diseased glycan pool and the control glycan pool with one or more exoglycosidases.

14. The method of embodiment 1, further comprising amplifying and segregating the glycosylation marker by digesting the diseased glycan pool and the control glycan pool with an array comprising one or more exoglycosidases.

15. The method of embodiment 1, wherein the diseased glycan pool and the control glycan pool are pools of N-linked glycans.

16. The method of embodiment 15, wherein said releasing is releasing of N-glycans from a gel.

17. The method of embodiment 1, wherein the diseased glycan pool and the control glycan pool are pools of O-linked glycans.

18. The method of embodiment 1, wherein said releasing comprises attaching glycoproteins to polyvinyldene fluoride membranes.

19. The method of embodiment 18, wherein said releasing is releasing by ammonia-based β-elimination from the polyvinyldene fluoride membranes.

20. The method of embodiment 1, further comprising labeling glycans in the diseased glycan pool and the control glycan pool with a radioactive or fluorescent label.

21. The method of embodiment 20, wherein the fluorescent label is 2-aminopyridine, 2-aminobenzamide, 2-aminoanthranilic acid, 2-aminoacridone or 8-aminonaphthalene-1,3,6-trisulfonic acid.

22. The method of embodiment 20, wherein the fluorescent label is 2-aminobenzamide.

23. The method of embodiment 1, wherein the diseased sample and the control sample are samples of a body fluid.

24. The method of embodiment 23, wherein the body fluid is whole serum, blood plasma, urine, seminal fluid or saliva.

25. The method of embodiment 23, wherein the body fluid is whole serum.

26. A method for diagnosing and monitoring cancer in a subject comprising
obtaining a sample of body fluid or a body tissue of the subject;
releasing a glycan pool of total glycoproteins from the sample without purifying the glycoproteins;
measuring a glycoprofile of the glycan pool.

27. The method of embodiment 26, further comprising determining a clinical status of the subject from a level of a glycosylation marker of cancer in the glycoprofile.

28. The method of embodiment 27, wherein the clinical status is a stage of cancer.

29. The method of embodiment 27, wherein the clinical status is selected from the group consisting of cancer, precancerous condition, a benign condition or no condition.

30. The method of embodiment 26, wherein cancer is pancreatic cancer, prostate cancer, breast cancer, hepatocellular carcinoma, ovary cancer, bladder cancer, renal cancer, colon cancer, stomach cancer or lung cancer.

31. The method of embodiment 26, wherein cancer is hepatocellular carcinoma.

32. The method of embodiment 31, wherein the glycosylation marker is a percentage of core fucosylated glycans measured after digestion with α2-3,6,8-sialidase, β1-4 galactosidase and β-N-acetylglucosaminidase in the glycans.

33. The method of embodiment 26, wherein cancer is prostate cancer.

34. The method of embodiment 26, wherein cancer is breast cancer.

35. The method of embodiment 26, wherein cancer is ovarian cancer.

36. The method of embodiment 26, wherein cancer is pancreatic cancer.

37. The method of embodiment 26, wherein the body fluid is whole serum, blood plasma, urine, seminal fluid or saliva.

38. The method of embodiment 26, wherein the body fluid is serum.

39. The method of embodiment 26, wherein releasing a glycan pool comprises preparing a gel from the sample.

40. The method of embodiment 39, wherein the glycan pool is a pool of N-glycans and releasing a glycan pool further comprises releasing the pool of N-glycans from the gel using PNGase F enzyme.

41. The method of embodiment 26, wherein releasing the glycan pool comprises attaching the total glycoproteins to polyvinyldene fluoride membranes.

42. The method of embodiment 41, wherein the glycan pool is a pool of N-glycans and releasing the glycan pool further comprises incubating the polyvinyldene fluoride membranes with PNGaseF enzyme.

43. The method of embodiment 41, wherein releasing the glycan pool further comprises chemically releasing the glycan pool by β-elimination 44. The method of embodiment 41, wherein releasing the glycan pool further comprises releasing the glycan pool by ammonia-based β-elimination.

45. The method of embodiment 26, further comprising digesting the glycans with one or more exoglycosidase.

46. The method of embodiment 26, further comprising sequential digesting the glycans with one or more exoglycosidase.

47. The method of embodiment 26, further comprising digesting the glycans with an array comprising more than one exoglycosidase.

48. The method of embodiment 26, wherein measuring the glycoprofile is carried out by chromatography, mass spectrometry or a combination thereof.

49. A method for optimizing a dosage of a existing therapeutic agent against cancer comprising
obtaining a first sample of a body fluid or a body tissue from a cancer patient before administering the therapeutic agent to the patient;
obtaining a second sample of a body fluid or a body tissue from the cancer patient after administering the therapeutic agent to the patient;
releasing glycans of glycoproteins from the first and the second samples without purifying the glycoproteins and without exposing the first and the second sample to hydrazinolysis;
measuring a first glycoprofile of the glycans from the first sample and a second glycoprofile of the glycans from the second sample;
comparing a level of a glycosylation marker of the cancer in the first glycoprofile and the second glycoprofile.

50. A method of testing a new therapy or a new therapeutic agent for treating cancer comprising
obtaining a first sample of a body fluid or a body tissue from a cancer patient before exposing the patient to the new therapy or the new therapeutic agent;
obtaining a second sample of a body fluid or a body tissue from the cancer patient after exposing the patient to the new therapy or the new therapeutic agent;
releasing glycans of glycoproteins from the first and the second samples without purifying the glycoproteins and without exposing the first and the second samples to hydrazinolysis;
measuring a first glycoprofile of the glycans from the first sample and a second glycoprofile of the glycans from the second sample;
comparing a level of a glycosylation marker of the cancer in the first glycoprofile and the second glycoprofile.

51. A database comprising
glycan structures of glycans of glycoproteins, wherein the glycans are released from a sample of a body fluid or a body tissue of a subject diagnosed with cancer and wherein releasing the glycans is carried out without purifying the glycoproteins.

52. The database of embodiment 49, wherein the glycans are N-glycans.

53. The database of embodiment 49, wherein the glycans are O-glycans.

What is claimed is:

1. A method of identifying and/or quantifying one or more glycosylation markers of a cancer, comprising
   (A) obtaining a glycoprotein-containing sample from a subject diagnosed with the cancer, wherein the glycoprotein-containing sample contains plural types of glycoproteins;
   (B) immobilizing total glycoproteins of the sample from the subject on a protein binding membrane or in a gel without having isolated or purified specific glycoproteins of the sample;
   (C) releasing glycans of the total immobilized glycoproteins on the protein binding membrane or in the gel without the gel having been separated into a plurality of bands prior to said releasing;
   (D) washing the protein binding membrane or the gel to separate the released glycans from parent proteins immobilized on the protein binding membrane or in the gel;
   (E) measuring a glycosylation profile of the released glycans; and
   (F) comparing the glycosylation profile with a control profile to determine the one or more glycosylation markers of the cancer.

2. The method of claim 1, wherein the subject is a human.

3. The method of claim 1, wherein the sample is a sample of a body fluid of the subject.

4. The method of claim 3, wherein the body fluid is whole serum, blood plasma, urine, seminal fluid, seminal plasma, pleural fluid, ascites, nipple aspirate, feces or saliva.

5. The method of claim 4, wherein the body fluid is whole serum.

6. The method of claim 1, wherein the cancer is pancreatic cancer, prostate cancer, breast cancer, hepatocellular carcinoma, ovarian cancer, bladder cancer, renal cancer, colon cancer, stomach cancer, lung cancer or uveal melanoma.

7. The method of claim 1, further comprising digesting the glycans with one or more exoglycosidases to amplify and/or segregate the one or more glycosylation markers.

8. The method of claim 7, wherein said digesting is sequential digesting.

9. The method of claim 7, wherein said digesting is digesting with an array comprising one or more exoglycosidases.

10. The method of claim 7, further comprising making preliminary and/or final assignments of the structures of the glycans using a database.

11. The method of claim 7, wherein the glycosylation marker comprises one or more digested glycans.

12. The method of claim 1, wherein the released glycans are N-linked glycans.

13. The method of claim 1, wherein said comparing comprises selecting a best glycosylation marker out of the one or more glycosylation markers, wherein the best glycosylation marker has a highest correlation with one or more parameters of the subject.

14. The method of claim 1, further comprising labeling the released glycans with a fluorescent label prior to measuring.

15. The method of claim 14, wherein the fluorescent label is 2-aminobenzamide.

16. A method of diagnosing breast cancer, comprising
   (A) obtaining a glycoprotein-containing sample from a subject in need thereof;
   (B) releasing N-linked glycans of the glycoproteins;
   (C) measuring an amount of released A3GF1 glycans;
   (D) comparing the amount of released A3G1F glycan with an amount of A3G1F glycan in a control sample from a control subject that does not have breast cancer; and
   (E) determining a clinical status of the subject, wherein a higher level of the A3G1F glycan in the sample of the subject than in the control sample indicates that the subject has breast cancer.

17. The method of claim 16, wherein the amount of A3G1F glycan is an amount of A3G1F glycan measured after digestion of the released glycans with an array comprising sialidase and β galactosidase.

18. The method of claim 16, further comprising measuring a ratio of an amount of A3G3S3F glycan to an amount of A3G3S3 glycan.

19. The method of claim 1, wherein the glycosylation profile of the glycans is measured using a quantitative analytical technique selected from at least one of chromatography, mass spectrometry and electrophoresis.

20. The method of claim 16, wherein the sample is a sample of a body fluid or a body tissue of the subject.

21. The method of claim 20, wherein the sample is a sample of whole serum of the subject.

22. The method of claim 1, wherein the sample is a sample of a body fluid or a body tissue of the subject.

23. The method of claim 1, wherein the released glycans are O-linked glycans.

24. The method of claim 16, further comprising immobilizing total glycoproteins of the sample from the subject on a protein binding membrane or in a gel prior to said releasing.

25. A method of monitoring breast cancer, comprising
   (A) obtaining a glycoprotein-containing sample from a subject in need thereof, wherein the sample is a second sample of the subject;
   (B) releasing N-linked glycans of the glycoproteins;
   (C) measuring an amount of released glycans;
   (D) comparing the amount of released A3G1F glycan with an amount of A3G1F glycan in a first sample from the subject obtained at an earlier time than said second sample; and
   (E) determining a clinical status of the subject wherein a higher level of the A3G1F glycan in the second sample than in the first sample indicates that the breast cancer has progressed in the subject since the first sample was obtained.

26. The method of claim 16, wherein the subject is human.

27. The method of claim 25, wherein the first and second samples are samples of whole serum of the subject.

28. The method of claim 25, further comprising immobilizing total glycoproteins of the sample from the subject on a protein binding membrane or in a gel prior to said releasing.

29. The method of claim 25, wherein the amount of A3G1F glycan is an amount of A3G1F glycan measured after digestion of the released glycans with an array comprising sialidase and β galactosidase.

30. The method of claim 24, wherein the immobilizing is immobilizing the total glycoproteins of the sample from the subject in a gel without the gel having been separated into a plurality of bands prior to said releasing.

31. The method of claim 28, wherein the immobilizing is immobilizing the total glycoproteins of the sample from the subject in a gel without the gel having been separated into a plurality of bands prior to said releasing.

32. A method of diagnosing breast cancer, comprising
   (A) obtaining a glycoprotein-containing sample from a subject in need thereof;
   (B) measuring an amount of a glycoprotein glycoform carrying A3G1F glycan in the sample;
   (C) comparing the amount of the glycoprotein glycoform carrying A3G1F glycan with an amount of the glycoprotein glycoform carrying A3G1F glycan in a control sample from a control subject that does not have breast cancer; and (D) determining a clinical status of the subject, wherein a higher level of the glycoprotein glycoform carrying A3G1F glycan in the sample of the subject than in the control sample indicates that the subject has breast cancer.

33. A method of monitoring breast cancer, comprising (A) obtaining a glycoprotein-containing sample from a subject in need thereof, wherein the sample is a second sample of the subject;

(B) measuring an amount of a glycoprotein glycoform carrying A3G1F glycan in the sample;

(C) comparing the amount of the glycoprotein glycoform carrying A3G1F glycan with an amount of the glycoprotein glycoform carrying A3G1F glycan in a first sample from the subject obtained at an earlier time than said second sample; and (D) determining a clinical status of the subject wherein a higher level of the glycoprotein glycoform carrying A3G1F glycan in the second sample than in the first sample indicates that the breast cancer has progressed in the subject since the first sample was obtained.

* * * * *